United States Patent [19]

Kamiya et al.

[11] 4,267,340

[45] * May 12, 1981

[54] DISULFIDE SUBSTITUTED OXAZETIDINE DERIVATIVES

[75] Inventors: Takashi Kamiya, Suita; Yoshihisa Saito, Takarazuka; Tsutomu Teraji, Hirakata; Osamu Nakaguti, Nagaihigashi; Teruo Oku, Shinmachi, Hitoshi Nakamura, Masashi Hashimoto, both of Tayonaka, all of Japan

[73] Assignee: Fujisawa Pharmaceutical Co., Ltd., Osaka, Japan

[*] Notice: The portion of the term of this patent subsequent to Jan. 31, 1995, has been disclaimed.

[21] Appl. No.: 852,053

[22] Filed: Nov. 16, 1977

Related U.S. Application Data

[60] Division of Ser. No. 711,980, Aug. 5, 1976, Pat. No. 4,071,527, which is a division of Ser. No. 430,688, Jan. 4, 1974, Pat. No. 3,993,646, which is a continuation-in-part of Ser. No. 266,470, Jun. 26, 1972, abandoned.

[30] Foreign Application Priority Data

| Jun. 24, 1971 | [JP] | Japan | 46-46158 |
| Aug. 14, 1971 | [JP] | Japan | 46-61776 |
| Aug. 14, 1971 | [JP] | Japan | 46-61777 |
| Aug. 18, 1971 | [JP] | Japan | 46-62687 |
| Aug. 21, 1971 | [JP] | Japan | 46-63885 |
| Aug. 21, 1971 | [JP] | Japan | 46-63886 |

[51] Int. Cl.$^3$ .............. C07D 277/20; C07D 263/30
[52] U.S. Cl. ........................ 548/187; 548/186; 548/152; 548/225; 548/228; 548/217; 548/336; 548/337; 548/374; 544/333; 544/367; 544/405; 424/246

[58] Field of Search ............. 260/307 D, 239 AL; 548/187, 186, 152, 225, 228, 217, 336, 337, 374; 544/333, 367, 405

[56] References Cited

U.S. PATENT DOCUMENTS

| 2,926,160 | 2/1960 | Kern | 260/307 D |
| 3,840,556 | 10/1974 | Kukolja | 260/239 AL |
| 3,862,164 | 1/1975 | Cooper | 544/16 |
| 3,872,086 | 3/1975 | Barton et al. | 544/16 |
| 3,927,013 | 12/1975 | Barton et al. | 260/239 AL |
| 3,953,424 | 4/1976 | Barton et al. | 544/18 |
| 3,991,069 | 11/1976 | Barton et al. | 260/239 AL |
| 3,993,646 | 11/1976 | Kamiya et al. | 544/18 |
| 4,036,835 | 7/1977 | Fuglio et al. | 544/18 |
| 4,091,210 | 5/1978 | Kamiya et al. | 260/239 AL |

Primary Examiner—Nicholas S. Rizzo
Attorney, Agent, or Firm—Oblon, Fisher, Spivak, McClelland & Maier

[57] ABSTRACT

An oxoazetidine derivative compound of the formula:

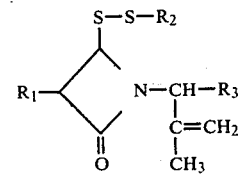

wherein $R_1$ represents a substituted or unsubstituted amino radical and $R_3$ represents a radical selected from the group consisting of carboxy, protected carboxy, ester, acid amide, acid anhydride, acid halide, acid azide and carboxy salt, and $-SR_2$ is a residue of a thiophilic sulphur nucleophile.

13 Claims, No Drawings

DISULFIDE SUBSTITUTED OXAZETIDINE DERIVATIVES

CROSS REFERENCES TO RELATED APPLICATIONS

This is a division, of application Ser. No. 711,980, filed Aug. 5, 1976 U.S. Pat. No. 4,071,527, which is a division of application Ser. No. 430,688, filed Jan. 4, 1974, now U.S. Pat. No. 3,993,646, which is a C-I-P of application Ser. No. 266,470, filed June 26, 1972, now abandoned.

BACKGROUND OF THE INVENTION

1. Field of the Invention

This invention relates generally to a method for producing antibacterially active cepham and cephem derivatives, to antibacterially active penam derivatives, which are also useful as intermediate compounds in said process, and further to antibacterically active oxoazetidine derivatives which are useful as intermediates in said process and which further exhibit useful antibacterial properties. More particularly, this invention relates to a process for producing cephem derivatives having antibacterial activity from penam type compounds, which involves: (1) a unique oxidation procedure for oxidizing penam derivatives, (2) a unique reaction procedure involving said oxidized penam derivatives with a thiophilic sulfur nucleophile, to produce new oxoazetidine derivatives having antibacterial activity, which may further be reacted to produce unique base reaction products thereof, (3) a unique process involving halogenation of said oxoazetidine derivatives or base reaction products thereof, to produce unique halogenated cepham or penam derivatives, possessing antibacterial activity, (4) to a unique process for producing antibacterially active 3- and 2-cephem derivatives from said halogenated intermediates, and (5) to an alternative process for producing halogenated penam and cepham derivatives by direct halogenation of said oxidized penam derivative.

2. Description of the Prior Art:

3- and 2-cephem derivatives of the type (I):

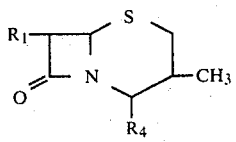

wherein $R_1$ is an amino or a substituted amino radical, and $R_4$ is hydrogen, or $R_3$ as will be defined below, and wherein the dotted lines indicate the alternative bond structure to provide the 3-cephem or 2-cephem isomers, are known in the prior art as possessing favorable antibacterial activity toward both gram-positive and gram-negative type bacteria. Its activity is recognized as being higher than most antibacterial compounds, yet it does not cause undesirable contraindications when administered to human beings, as do the more commonly available antibacterial compounds, such as penicillin. Heretofore, however, the reported methods for producing such cephem derivatives have proven to be generally disadvantageous from an industrial point of view because the obtainable yield of product was low and required rather complex isolation and purification procedures. The overall process techniques were therefore unduly costly, such that the product was economically uncompetitive with commercially available antibacterial compounds of lesser physiological activity.

It was first contemplated to prepare cephem derivatives from Cephalosporin C. However, the use of such a reactant was considered undesirable because it was quite expensive to obtain. It was later widely reported that cephem derivatives could be produced from the more inexpensive and more readily available penam compounds. However, the reported processes generally resulted in low yields and a generally impure product, and hence were incapable of producing a product which could be economically competitive with the prior art antibacterial compounds.

The process for preparing 7-amino(or acylamio)-3-methyl-3-cephem-4-carboxylic acid or its ester by rearrangement of the corresponding 6-amino (or acylamino)-2,2-dimethylpenam-3-carboxylic acid-1-oxide or its ester is already known. For instance, it is known to produce cephem derivatives of the type 7-amino (or acylamino)-3-methyl-3-cephem-4-carboxylic acid or its ester under acidic conditions (South African Pat. No. 67-1260, Belgian Pat. No. 747,382, Belgian Pat. No. 745,845, British Pat. No. 1204394, British Pat. No. 1,204,972 and U.S. Pat. No. 3,275,626), or in the presence of an acidic catalyst (Belgian Pat. No. 747,118 and French Pat. No. 2020209), or in the presence of a rearranging catalyst such as a base and a silyl halide (Belgian Pat. No. 763,104) or by use of a salt formed from a nitrogenous base and an acid (Belgian Pat. No. 747,119). It is also known to produce 7-(2-phenoxyacetamido)-3-methyl-3-cephem by heating 6-(2-phenoxyacetamido)-2,2-dimethylpenam-3-carboxylic acid-1-oxide at a temperature of from 100°–175° C. under acidic conditions. (See U.S. Pat. No. 3,275,626.) None of these processes, however, have proven to be entirely successful from the commercial point of view, and hence a need continues to exist for a more inexpensive technique for producing cephem derivatives whereby the product can be obtained in high yields and in good purity without the necessity of using difficulty obtainable special reagents.

One of the difficulties with producing cephem derivatives from penam derivatives, according to the prior art processes, is that it is difficult to obtain high yields of the oxide of the penam derivative, which is the necessary starting reactant for the prior art rearrangement reactions. Accordingly, it would be quite desirable to provide a method for producing such oxides of penam derivatives in high yields and good purity, which can then be subjected to rearrangement reactions to obtain high yields of the useful cephem derivative compounds.

It is, of course, well known that penam derivatives, such as penicillin, possess useful antibacterial activity. However, one difficulty with the preparation of penam derivative compounds for this purpose is that they must be purified to a relatively high degree, and the process of such purification is somewhat complex. Although a multitude of purification procedures have been reported in the prior art, none have proven to be entirely satisfactory, and other alternatives are continually being sought. It would be desirable, therefore, to provide a method of converting penam derivatives in their impure state to other, more easily isolatable products, which can be administered directly into the body, wherein they might be used per se as antibacterial compounds, or wherein they might be reconverted into an available form of the penam derivative compounds.

The penam nomenclature for the penicillins is described by Sheehan, Henery-Logan, and Johnson in the J. Am. Chem. Soc., 75,3294, footnote 2 (1953), and has been adapted to the cephalosporins by Morin, Jackson, Flynn, and Roeske in the J. Am. Chem. Soc., 84,3400 (1962). In accordance with these systems of nomenclature, "penam" and "cepham" refer respectively to the following saturated ring structures:

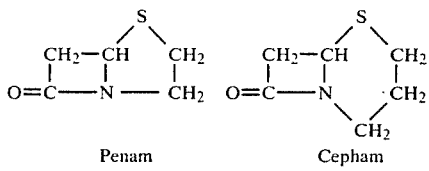

Penam    Cepham while "penem" and "cephem" refer to the same ring structure with a double bond.

SUMMARY OF THE INVENTION

Accordingly, it is one object of this invention to prepare antibacterially active cephem derivative compounds from penam derivative compounds, such as penicillin, in high yields and at generally high levels of purity.

It is another object of this invention to provide a process for oxidizing penam derivative compounds to provide high yields of oxidized products which can be further used as intermediates in the formation of other types of antibacterially active compounds and/or for producing antibacterially active cepham and cephem derivative compounds.

It is a further object of this invention to produce oxoazetidine derivative compounds which exhibit antibacterial properties, which can also be used as intermediates for the production for novel penam, cepham derivatives, and antibacterially active cephem derivatives.

A still further object of this invention is to produce antibacterially active bis-oxoazetidine derivative compounds which can be used as intermediates for the production of novel cepham and penam derivative compounds and for producing 2- or 3-cephem derivative compounds.

A still further object of this invention is to provide a method of producing novel antibacterially active halogenated penam derivative compounds and novel, antibacterially active halogenated cephem derivative compounds.

Another object of this invention is to provide a method of forming 2- and 3-cephem derivative compounds from said halogenated penam and halogenated cepham derivative compounds.

A further object of this invention is to provide a method for producing said halogenated penam and cepham derivative compounds from said oxidized penam derivative compounds.

These and other objects, as will hereinafter become more readily apparent, have been provided by:

an oxoazetidine derivative compound of the formula:

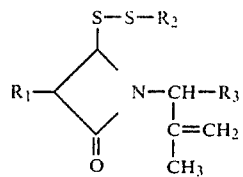

wherein $R_1$ represents a substituted or unsubstituted amino radical and $R_3$ represents a radical selected from the group consisting of carboxy, protected carboxy, ester, acid amide, acid anhydride, acid halide, acid azide and carboxy salt, and $-SR_2$ is a residue of a thiophilic sulphur nucleophile.

DETAILED DESCRIPTION OF PREFERRED EMBODIMENTS

The present process can provide a cephem derivative of the formula:

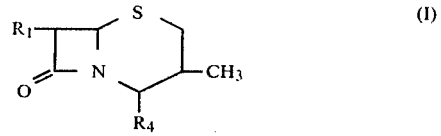

(I)

wherein $R_1$ is a substituted or unsubstituted amino radical. Suitable substituted amino radicals include acyl substituted and other amino protecting group substitution. Suitable acyl substitution groups include the aliphatic acyl radicals and acyl radicals containing an aromatic or heterocyclic ring. Among the suitable aliphatic acyl radicals include the saturated or unsaturated alkanoyl radicals which may be branched or which may contain a cyclic ring, such as the aliphatic acyl radicals, for example, formyl, acetyl, propionyl, butyryl, isobutyryl, valeryl, isovaleryl, pivaloyl, acryloyl, crotonoyl, 2-methylacryloyl, cyclopentylcarbonyl, cyclohexylcarbonyl, cycloheptylcarbonyl, cyclohexylacetyl, cycloheptylacetyl, cyclohexylpropionyl, cycloheptylpropionyl, dihydrobenzoyl, 2,4,6-cycloheptatrienylacetyl, dihydrophenylacetyl, etc., and the saturated or unsaturated alkanoyl radicals containing oxygen or sulphur, for example, methoxyacetyl, methylthioacetyl, 2-propenylthioacetyl, cyclohexylthioacetyl, cyclohexyloxyacetyl, dihydrophenoxyacetyl, dihydrophenylthioacetyl, cyclopentyloxycarbonyl, cyclohexyloxycarbonyl, dihydrophenoxycarbonyl, cycloheptyloxycarbonyl, etc. Suitable acyl radicals containing an aromatic ring include, for example, the aryloyl (e.g., benzoyl, toluoyl, naphthoyl, α-methylnaphthoyl, phthaloyl, tetrahydronaphthoyl, etc.) or the aralkanoyl (e.g., phenylacetyl, phenylpropionyl, phenylbutyryl, tolylacetyl, xylylacetyl, naphthylacetyl, tetrahydronaphthylacetyl, etc.) radicals. The carbon atom in the alkyl moiety of the said aralkanoyl radical may be replaced with an oxygen or sulphur atom, for example, phenoxyacetyl, benzyloxycarbonyl, xylyloxycarbonyl, naphthoxycarbonyl, phenoxycarbonyl, 2-phenoxypropionyl, 2-phenoxybutyryl, etc. The heterocyclic ring of the said acyl radical may be saturated or unsaturated, monocyclic or polycyclic, and may contain at least one heteroatom, such as an oxygen, sulphur, nitrogen atom or the like, and particularly thiophene, benzothiophene, furan, pyran, isobenzofuran, cromene, xanthene, 2H-pyrrole, 3H-pyrrole, pyrrole, imidazole, pyrazole, pyridine, pyrimidine, pyrazine, pyridazine, isoindole, indole, indazole, quinoline, isoquinoline, isoxazole, oxadiazole, pyrrolidine, pyrroline, imidazolidine, piperidine, piperadine, diazole, triazole, oxazole, thiazole, thiadiazle, tetrazole, benzoxazole, benzoxadiazole, benzothiazole, benzothiadiazole, benzotriazole, benzimidazole, etc. Examples of the said acyl radical which contain such heterocyclic rings are: 1H (or 2H)-tetrazolylacetyl, thienylacetyl, thienylpropionyl, furylacetyl, piperazinylacetyl, pyrrolidinylacetyl, pyrrolidinylpropionyl, benzothiazolylacetyl, oxazolylacetyl, benzoxazolylacetyl, etc. One or more carbon atoms in the alkyl moiety of these alkanoyls containing a heterocyclic ring may be replaced with an oxygen or sulphur atom, such as: pyridylmethoxycarbonyl, 2-furyloxycarbonyl, 8-quinolyloxycarbonyl, or the like. Further, the aliphatic acyl radical and the acyl radical containing an aromatic or heterocyclic ring may have appropriate substituents such as an alkyl (e.g., methyl, ethyl, propyl, isopropyl, 1-propenyl, 2-propenyl, cyclopropyl, cyclopentyl, cyclohexyl, cycloheptyl, etc.), alkoxy (e.g., methoxy, ethoxy, propoxy, isopropoxy, etc.), alkylthio (e.g., methylthio, ethylthio, etc.), aryl (e.g., phenyl, xylyl, tolyl, etc.), aralkyl (e.g., benzyl, phenethyl, etc.), amino, mercapto, nitro, carboxy or hydroxy radicals or a halogen (e.g., chlorine, bromine, fluorine, etc.). Exemplary of such acyl radicals include: trichloroethoxycarbonyl, tribromoethoxycarbonyl, 1-cyclopropylethoxycarbonyl, chloroacetyl, 2-chloropropionyl, trifluoroacetyl, phenylglycyl, p-aminophenylacetyl, p-nitrobenzyloxycarbonyl, o-bromobenzyloxycarbonyl, o-nitrobenzyloxycarbonyl, p-methoxybenzyloxycarbonyl, 3,4-dimethoxybenzyloxycarbonyl, p-hydroxyphenylacetyl, 2,6-dimethoxybenzoyl, 3-phenyl-5-methyl-4-oxazolylcarbonyl, 3-(2-chlorophenyl)-5-methyl-4-oxazolylcarbonyl, 3-(2,6-dichlorophenyl)-5-methyl-4-oxazolylcarbonyl, 3-(2-chloro-6-fluorophenyl)-5-methyl-4-oxazolylcarbonyl, or the like. If the acyl radical contains a functional radical, such as an amino, hydroxy, mercapto, carboxy, etc., the functional radical may be protected with an appropriate protective radical. Suitable protective radicals for the amino radical include any of the conventional protective radicals, such as those acyl radicals which can easily be split off, such as trichloroethoxycarbonyl, tribromoethoxycarbonyl, benzyloxycarbonyl, p-toluenesulfonyl, p-nitrobenzyloxycarbonyl, o-bromobenzyloxycarbonyl, o-nitrophenylsulfenyl, chloroacetyl, trifluoroacetyl, formyl, tert-butoxycarbonyl, p-methoxybenzyloxycarbonyl, 3,4-dimethoxybenzyloxycarbonyl, 4-phenylazobenzyloxycarbonyl, 4-(4-methoxyphenylazo)benzyloxycarbonyl, pyridine-1-oxide-2-methoxycarbonyl, 2-pyridylmethoxycarbonyl, 2-furyloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl, or other radicals which can easily be split off, such as trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene (among these, 1-methoxycarbonyl-2-propylidene and 2-ethoxycarbonylcyclohexylidene radicals may be representable as 1-methoxycarbonyl-1-propene-2-yl and 2-ethoxycarbonyl-1-cyclohexenyl radical, respectively), mono or disilyl, etc. Suitable protective radicals for the hydroxy or mercapto radicals include any of the conventional protective radicals for hydroxy or mercapto radicals such as the acyl radicals which can be easily split off, such as benzyloxycarbonyl, 4-nitrobenzyloxycarbonyl, 4-methoxybenzyloxycarbonyl, 3,4-dimethoxybenzyloxycarbonyl, 4-phenylazobenzyloxycarbonyl, 4-(4-methoxyphenylazo)benzyloxycarbonyl, tert-butoxycarbonyl, 1,1-dimethylpropoxycarbonyl, isopropoxycarbonyl, diphenylmethoxycarbonyl, 2-pyridylmethoxycarbonyl, 2,2,2-trichloroethoxycarbonyl, 2,2,2-tribromoethoxycarbonyl, 3-iodopropoxycarbonyl, 2-furfuryloxycarbonyl, 1-adamantyloxycarbonyl, 1-cyclopropylethoxycarbonyl, 8-quinolyloxycarbonyl, trifluoroacetyl, etc., and those radicals which can be easily split off, other than acyl radicals, such as benzyl, trityl, methoxymethyl, 2-nitrophenylthio, 2,4-dinitrophenylthio, etc. The protective radical for the carboxy radical may be any of those conventional protective radicals used for protecting a carboxy radical, such as an ester group, such as methyl, ethyl, propyl, isopropyl, tert-butyl, butyl, benzyl, diphenylmethyl, triphenylmethyl, p-nitrobenzyl, p-methoxybenzyl, benzoylmethyl, acetylmethyl, p-nitrobenzoylmethyl, p-bromobenzoylmethyl, p-methanesulfonylbenzoylmethyl, phthalimidomethyl, trichloroethyl, tribromoethyl, 1,1-dimethyl-2-propynyl, acetoxymethyl, propionyloxymethyl, pivaloyloxymethyl, 1,1-dimethylpropyl, 1,1-dimethyl-2-propenyl, 3-methyl-3-butenyl, succinimidomethyl, 1-cyclopropylethyl, 3,5-di(tert)butyl-4-hydroxybenzyl, methylsulfenylmethyl, phenylsulfenylmethyl, methylthiomethyl, phenylthiomethyl, dimethylaminomethyl, quinoline-1-oxide-2-methyl, pyridine-1-oxide-2-methyl, di(p-methoxyphenyl)methyl ester, etc., the silyl ester groups derived from a silyl compound, such as dimethyldichlorosilane, etc., which have been reported in Japanese Patent Application No. 7332/1971, laid open to public inspection under No. 7073/1971 and in Netherlands Patent Application which has been laid open to public inspection under No. 7105259, and non-metallic compounds at the carboxy radical derived from such non-metallic compounds as titanium tetrachloride, etc., which have been reported in German Offenlegungsschrift No. 2062925. The amino protective radical other than an acyl radical which is mentioned in the substituted amino radical for $R_1$ is the same as that which is exemplified as the protective radical for the amino radical in the acyl radical.

$R_4$ of formula (I) above, may be hydrogen or $R_3$ which is defined as a carboxy radical or a protected carboxy radical, wherein the protecting group is a silyl or non-metallic radical such as those indicated above as being useful as protecting groups for the carboxy radical. $R_4$ may also be: (1) an ester; a saturated or unsaturated alkyl (e.g., methyl, ethyl, propyl, isopropyl, butyl, tert-butyl, cyclohexyl, cycloheptyl, vinyl, 1-propenyl, 2-propenyl, 3-butenyl, etc.) ester, aryl (e.g., phenyl, xylyl, tolyl, naphthyl, etc.) ester, aralkyl (e.g., benzyl, phenethyl, etc.) ester, or an ester wherein one of the carbon atoms of the alkyl moiety is replaced with a nitrogen sulphur or oxygen atom, or by a carbonyl radical such as methoxymethyl ester, ethoxymethyl ester, methylthioethyl ester, methylthiomethyl ester, dimethylaminoethyl ester, diethylaminoethyl ester, phenoxymethyl ester, phenylthiomethyl ester, methylsulfenylmethyl ester, phenylsulfenylmethyl ester benzoylmethyl ester, toluoylmethyl ester, etc. or an ester containing one or more appropriate substituents (e.g., halogen, alkoxy, alkanesulfonyl, phenylazo, etc.) such as chloromethyl ester, bromomethyl ester, trichloroethyl ester, cyanomethyl ester, p-nitrophenyl ester, 2,4,5-trichlorophenyl ester, 2,4,6-trichlorophenyl ester, pentachlorophenyl ester, p-methanesulfonylphenyl ester, 4-phenylazophenyl ester, 2,4-dinitrophenyl ester, p-chlorobenzyl ester, o-nitrobenzyl ester, p-methoxybenzyl ester, p-nitrobenzyl ester, 3,4,5-trimethoxybenzyl ester, bis(p-methoxyphenyl)methyl ester, pentachlorobenzyl ester, trichlorobenzyl ester, 3,5-di(tert)butyl-4-hydroxybenzyl ester, p-nitrophenylthiomethyl ester, p-nitrobenzoylmethyl ester, p-chlorobenzoylmethyl ester, etc., or an ester formed from a thioalcohol, a substituted thioalcohol, N-hydroxysuccinimide, N-hydroxyphthalimide, tetrahydrofuran, 1-cyclopropylethanol, 1-phenyl-3-methyl-5-pyrazolone, 3-hydroxypyridine, 2-hydroxymethylpyridine-1-oxide, 1-hydroxy-2(1H)-pyridine, dimethylhydroxyamine, diethylhydroxyamine, glycolamide, 8-hydroxyquinoline, 2-hydroxymethylquinoline-1-oxide, oxime, methoxyacetylene, ethoxyacetylene, tert-butylethynyldimethylamine, tert-butylethynyldiethylamine, ethylethynyldiethylamine, 2-ethyl-5-(3-sulfophenyl)isoxazolium hydroxide inner salt or the like;

(2) An acid amide: an N-alkyl acid amide (e.g., N-methyl acid amide, N-ethyl acid amide, etc.), N,N-dialkyl acid amide (e.g., N,N-dimethyl acid amide, N,N-diethyl acid amide, N-methyl-N-ethyl acid amide, etc.), or an acid amide with imidazole, 4-substituted imidazole, etc.;

(3) An acid anhydride; an acid anhydride with a dialkyl phosphate, dibenzyl phosphate, phosphoric acid, sulfuric acid, alkyl carbonate, aliphatic carboxylic acid, (e.g., pivalic acid, pentanoic acid, isopentanoic acid, 2-ethylbutanoic acid, chloroacetic acid, crotonic acid, valeric acid, propionic acid, 3-chloro-2-pentanoic acid, 3-bromo-2-buteneoic acid, phenylacetic acid, phenoxyacetic acid, furaneacetic acid, thiopheneacetic acid, etc.), aromatic carboxylic acid (e.g., benzoic acid, etc.) or the like, or a symmetric acid anhydride;

(4) An acid halide; acid chloride, acid bromide, etc.

(5) An acid azide;

(6) A carboxy salt; acid salt with a metal (e.g. sodium, potassium, magnesium, etc.) or an organic amine (e.g. methylamine, diethyl amine, trimethylamine, aniline, pyridine, picoline, N,N'-dibenzylethylenediamine, etc.)

The halogenated derivative reactant of this invention can be formed by several techniques. In one technique, a penam compound of the formula (II)

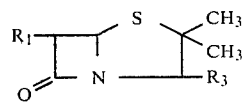

wherein $R_1$ and $R_3$ are as defined above, is oxidized to the corresponding oxidized penam derivative of the formula (III):

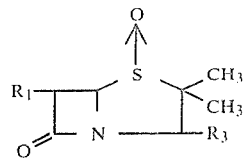

wherein $R_1$ and $R_3$ are as defined above.

Although this reaction is known in the prior art, the yield of obtainable oxidized product, heretofore, has been quite low. Moreover, with certain penams, such as 6-(2-phenylacetamido)-2,2-dimethylpenam-3-carboxylic acid, oxidation has not been successfully performed, even to a limited extent (see *Chemistry Of Penicillin*, Page 152, published by Princeton University Press, Princeton, N.J., 1949).

According to the methods known in the art, if the starting compound of this oxide reaction contains a free amino radical in its molecule, it is necessary to protect the amino radical with an appropriate protective group. Otherwise, the oxide reaction will result in poor yields. For instance, the oxidation yield of 6-phenylglycylamino-2,2-dimethylpenam-3-carboxylic acid and 6-amino-2,2-dimethylpenam-3-carboxylic acid are respectively 25 to 8%, and even if the amino radical of the former compound is protected, the yield is still only 52% (*Journal Of Organic Chemistry*, Vol. 30, Page 4388(1965)).

The present invention has now alleviated the difficulties by the discovery that the oxidation reaction will occur with a higher degree of conversion, even with those penam derivatives previously considered to be non-oxidizable, if the oxidation reaction is conducted in the presence of a compound of a Group Vb or Vib metal of the Periodic Table, as a reaction catalyst. Suitable compounds which have been found to possess catalytic properties for the oxidation reaction include: tungstic acid, molybdic acid, vanadic acid, or the like, or the alkali metal (e.g., sodium, potassium or the like), alkaline earth metal (e.g., calcium, magnesium, or the like), or ammonium or organic acid salts thereof, or vanadium pentoxide.

Suitable oxidizing agents which can be used in this process include: the peracids, such as hydrogen peroxide, perbenzoic acid, m-chloroperbenzoic acid, percarbonic acid, periodic acid, or the like, or salts thereof, or the hydroperacids, or the like.

Whereas the prior art techniques were incapable of oxidizing 6-(2-phenylacetamido)-2,2-dimethylpenam-3-carboxylic acid, by using the catalyst in the techniques of the present invention, this penam derivative is now oxidizable. Moreover, even if the starting compound contains a free amino radical in the molecule, it need not be protected, as was previously considered to be necessary by the prior art, and yet good yields will be obtained. The oxide reaction can now be applied to other penam derivative compounds which have not heretofore been susceptible to oxidation.

The reaction is preferably carried out in an aqueous media or in a hydrophilic organic solvent, such as acetic acid, a lower alcohol, tetrahydrofuran, dioxane, dimethylformamide, acetone, dichloromethane, or the like, at temperatures of about room temperature or below. These reaction conditions are so mild that the reaction can successfully be conducted even with relatively unstable compounds, and the purity of the resulting product will be extremely high.

One of the unique discoveries of the present invention is that the oxidized penam derivatives, formed as described above, can be further reacted to form an oxoazetidine derivative having the formula (IV):

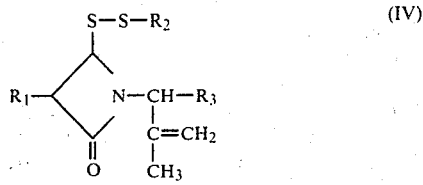

wherein $R_1$ and $R_3$ are as defined above, and $SR_2$ is a residue of a thiophilic sulphur nucleophile. These oxoazetidine derivatives have been found to not only be useful intermediates for further reaction, according to the methods of this invention, but they have also been found to possess significant and useful antibacterial properties. It is further believed that under certain conditions of use, when the oxoazetidine derivatives are administered to human beings, or to other animals, they may be reconverted back to the corresponding penam derivative form. It is therefore possible that these derivatives can be used instead of the corresponding penam derivative with significant advantage. As is well known, the isolation and purification of penam derivatives is quite complicated and costly, and it is possible that these difficulties can be circumvented by converting the penam derivative into its corresponding oxoazetidine derivative, which can be separated and purified quite simply and inexpensively, and use in that form. In order to convert the penam derivative into an oxoazetidine, the penam derivative must first be oxidized as discussed above, and then the oxide is reacted with a thiophilic sulphur nucleophile of the formula: $R_2$—SH, wherein $R_2$ may be a substituted or unsubstituted aliphatic, substituted or unsubstituted aromatic, or substituted or unsubstituted heterocyclic radicals. For instance, $R_2$ may be an alkyl radical, (e.g., methyl, ethyl, propyl, isopropyl, butyl, isobutyl, vinyl, 1-isopropenyl, 3-butenyl, or the like); a substituted alkyl radical (e.g., methoxymethyl, ethoxymethyl, benzyl, phenethyl, xylyl-methyl, p-chlorobenzyl, p-bromobenzyl, p-nitrobenzyl, p-methoxybenzyl, 2,4-dimethoxybenzyl, 2-chloro-4-methoxybenzyl, etc.); an aryl radical (e.g., phenyl, xylyl, tolyl, naphthyl, etc.); a substituted aryl radical (e.g., chloroethyl, nitrophenyl, bromophenyl, methoxyphenyl, dimethoxyphenyl, dichlorophenyl, chloronitrophenyl, etc.); a heterocyclic radical, which contains at least one hetero atom such as an oxygen, nitrogen, sulphur atom and the like (e.g., pyrrolidinyl, piperidyl, piperizinyl, homopiperazinyl, furyl, thienyl, pyrrolyl, pyridyl, imidazolizinyl, quinolyl, isoquinolyl, benzimidazolizinyl, benzothiazolyl, benzoxazolyl, thiazolyl, thiadiazolyl, thiatriazolyl, oxazolyl, oxadiazolyl, oxatriazolyl, triazolyl, tetrazolyl, etc.); a substituted heterocyclic radical wherein the heterocyclic radical is substituted with one or more appropriate substituents, such as an alkyl radical (e.g., methyl, ethyl, etc.), an alkoxy radical (e.g., methoxy, ethoxy, etc.), a halogen atom (e.g, fluorine, chlorine, bromine, etc.), a nitro radical, an aryl radical (e.g., phenyl, tolyl, xylyl, etc.), a substituted aryl radical (e.g., chlorophenyl, nitrophenyl, etc.), an aralkyl radical (e.g., benzyl, phenethyl, etc.) or the like; an acyl radical (e.g., acetyl, propionyl, benzoyl, phenylacetyl, thioacetyl, thiopropionyl, thiobenzoyl, phenylthioacetyl, heterocyclic thiocarbonyl, heteocyclic carbonyl, etc.). Of course, compounds which are capable of being converted into any of the above thiophilic sulphur nucleophiles under the reaction conditions can be used herein.

The reaction is preferably carried out in a solvent such as benzene, toluene, tert-butanol, isopropanol, methylisobutylketone, methylethylketone, dioxane, dimethylformamide, etc., or mixtures thereof, or mixtures with other inert solvents. The reaction is preferably carried out at a temperature of less than the boiling point of the solvent used, and preferably at between 50°–150° C. The thiophilic sulphur nucleophile may be used in at least an equivalent amount, although excess quantities are also permissible. The particular quantity to be used in a given reaction, of course, will depend upon the particular nucleophile used and the particular reactant and reactive conditions.

Although Belgian Pat. Nos. 770,726, 770,729, 770,730 and 770,731 broadly disclose isomers of the oxoazetidine derivatives of this invention, those isomers disclosed therein cannot be reacted further in the manner of the particular oxoazetidine derivatives of this invention, and they possess inferior antibiotic activity.

If $R_3$ of the above described oxoazetidine derivatives (IV) of this invention is a carboxy group, it can further be converted into the bis- form having the formula:

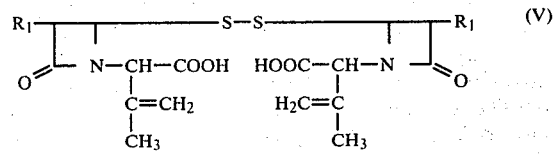

wherein $R_1$ is as defined above, by reaction in the presence of a base at room temperature, or with mild application of heat, in a suitable solvent. Suitable basic materials which can be used to effect this reaction include the alkali metals (e.g., sodium, potassium, etc.) hydroxides, the alkali metal carbonates, the alkali metal bicarbonates, the alkali metal alkoxides (e.g., potassium ethoxide, sodium ethoxide, etc.), silver oxide, trialkylamine (e.g., trimethylamine, triethylamine, etc.), N,N-dimethylaniline, N,N-dimethylbenzylamine, pyridine, or the like, or any of the conventional basic ion exchange resins. The reaction can be effected in an inert solvent, such as water, ethanol, isopropanol, tert-butanol, or the like.

The bis- derivatives of this invention are unique compounds which possess a significant antibiotic activity.

Of interest, is the observation that if $R_3$ of the oxoazetidine derivative (IV) is other than a carboxy group, under the same conditions of reaction, an undesirable isomer, which is unusable for further reaction according to the methods of this invention, and which possesses inferior antibacterial properties, is obtained. Accordingly, the bis-derivative is only obtainable if $R_3$ is a carboxy radical.

The oxoazetidine derivative of the formula (IV), or the bisoxoazetidine derivative of the formula (V) is then reacted with a halgenating agent to produce a dicyclic β-lactam of the formula:

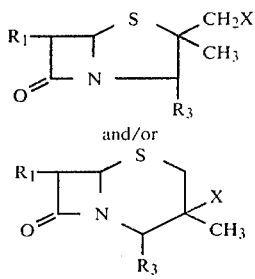

wherein $R_1$ and $R_3$ are as defined above, and X is a halogen atom, preferably bromine, chlorine or iodine.

Any halogenating reagent commonly used to cleave bonds between sulphur atoms may be used herein. For instance, suitable reagents include the halogens (e.g., bromine, chlorine, iodine, etc.), phosphorus pentachloride, thionylchloride, sulphur halide, sulphur dihalide, N-halosuccinimide (e.g., N-bromosuccinimide, N-iodosuccinimide, N-chlorosuccinimide, etc.), pyridinium hydrobromide perbromide (Fisher: *Reagent For Organic Synthesis*, Page 967), N-haloisocyanuric acid, phenyliododichloride, sulfenylhalide (e.g., benzothiazole-2-sulfenylchloride, benzothiazole-2-sulfenylbromide, benzenesulfenylchloride, benzenesulfenylbromide, o-nitrobenzenefulfenylchloride, quinoline-2-sulfenylchloride, quinoline-2-sulfenyliodide, 1,3,4-thiadiazole-2-sulfenylbromide, etc.), or the like.

The reaction is preferably carried out under mild conditions using a solvent such as acetonitrile, tetrahydrofuran, chloroform carbon disulfide, tetrachloroethane, ethylenechloride, benzene, toluene, dioxane, dimethylformamide, 1,2-dimethoxyethane, pyridine or the like. Of course, any inert solvent may also be employed. It is particularly preferable to conduct the reaction in the presence of an acid amide, such as acetamide, and, if desired, the reaction may further be carried out in the presence of a catalyst.

The relative quantities and selectivity for the halogenated compounds (VI) or (VII) will depend upon the particular oxoazetidine derivative, or bis- oxoazetidine derivative used. The rearrangement reaction from compound (VI) to compound (VII) will usually occur if the compound (VI) is allowed to stand at room temperature for an extended period. This reaction is accelerated, however, by the application of mild heat in the presence of a solvent such as acetonitrile, tetrahydrofuran, tert-butanol, isopropanol, benzene, dioxane, dimethylformamide, dimethylsulfoxide, pyridine or the like, or any other solvent inert to the reaction system.

The presence of a catalyst such as a Lewis acid or a Lewis base may further accelerate the reaction.

The halogenated products of the reaction are useful compounds per se, since they possess significant antibacterial activity. They are also useful as intermediates for the production of the cephem derivative compounds of the formula (I) according to the methods of this invention.

Alternatively, the halogenated compounds (VI) and (VII) may be prepared directly from the oxidized penam derivative (II) described above, without necessity of forming intermediate compounds (IV) or (V). In this instance, the oxidized penam derivative (II) is treated with a halogenating agent, which is capable of producing at least one halogen ion, in the presence of a nitrogenous base. Suitable such halogenating agents include hydrochloric acid, hydrobromic acid, hydroiodic acid, or the like.

Suitable nitrogenous base materials which may be used in the reaction include pyridine, picoline, collidine, quinoline, trimethylamine, triethlamine, ethyldicyclohexylamine, ethyldiisopropylamine, ammonia, aniline, N-methylaniline, N,N-dimethylaniline, N,N-diethylaniline, N-phenylmorpholine, N,N-dimethylbenzylamine or the like.

This reaction is preferably carried out in a solvent media such as acetonitrile, tetrahydrofuran, trichloroethane, benzene, dioxane, dichloroethane, tetrachloroethylene, dimethylformamide, dimethylsulfoxide, etc. Of course, other organic solvents which are inert to the reaction can also be employed.

In some instances, it is desirable to conduct the reaction in the presence of a quaternary ammonium or alkali metal (e.g., sodium, potassium, lithium, etc.) salt of the said hydrohalogenoic acid.

It is also possible to use a halogenating agent which is capable of producing a halogen ion in the form of a salt thereof with the nitrogenous base.

The nitrogenous base should be used in at least a stoichiometric amount, based on the halogenating agent, and particularly in a ratio of about 1 to 10 moles of base per mole of halogenating agent, and preferably 3.0 to 8.0 moles of base per mole of halogenating agent to achieve predominant yields.

The halogenating agent must be present in at least an amount sufficient to assure halogenation of one of the pendant methyl groups which is α to the sulphur atom in the heterocyclic ring.

Regardless of the reaction route used for forming the halogenated penam derivative (VI), or the halogenated cepham derivative (VII), these derivatives can be formed into the 2- or 3-cephem derivative compounds of the formula (I) by reaction with a dehydrohalogenoic acid reagent. Suitable dehydrohalogenoic acid reagents which may be used for this purpose include the alkali metal hydroxides (e.g., potassium hydroxide, sodium hydroxide, etc.), the alkali metal carbonates (e.g., potassium carbonate, sodium carbonate, etc.), the alkali metal bicarbonates (e.g., potassium bicarbonate, sodium bicarbonate, etc.), the alkali metal alkoxides (e.g., sodium ethoxide, potassium ethoxide, etc.), the alkali metal acetates (e.g., sodium acetate, potassium acetate, etc.), silver oxide, the trialkylamines (e.g., trimethylamine, triethylamine, ethyldicyclohexylamine, ethyldiisopropylamine, etc.), N,N-dimethylaniline, N-phenylmorpholine, N,N-dimethylbenzylamine, pyridine, picoline, collidine, quinoline, the quaternary ammonium salts (e.g., tetraethylammonium chloride, benzyltrimethylammonium mesitoate, etc.), the basic ion exchange resins, the lithium halides (e.g., lithium chloride, lithium bromide, etc.) or the like. The reagent should be used in at least an equimolar amount based on the reactants. If the reaction media contains an excess of base, the 2-cephem derivative isomer will be produced in preference to the 3-cephem derivative isomer.

The reaction is preferably carried out under the application of heat in a solvent such as acetonitrile, tetrahydrofuran, chloroform, carbon disulfide, tetrachloroethane, ethylenechloride, benzene, toluene, dioxane, dimethylformamide, 1,2-dimethoxyethane, pyridine or the like.

If the dehydrohalogenoic acid reagent used is a liquid, it can serve the dual function of reagent and solvent.

If $R_3$ of the cepham or penam derivative of formulas (VI) or (VII) is a carboxy radical, that carboxy radical must be protected during the reaction to prevent decarboxylation from occurring simultaneously with the primary reaction, unless it is desired to obtain a cephem derivative product wherein $R_4$ is a hydrogen atom.

Having now generally described the invention, a further understanding can be attained by reference to certain specific examples which are provided herein for purposes of illustration only and are not intended to be construed as limiting unless otherwise so indicated.
Reaction of:

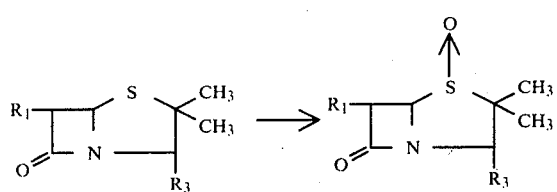

EXAMPLE 1

Sodium tungstate dihydrate (500 mg.) was added to a solution of 2,2,2-trichloroethyl 6-(2-phenylacetamido)-2,2-dimethylpenam-3-carboxylate (31.5 g.) in acetic acid (150 cc.), and to the mixture was added, dropwise, 30% hydrogen peroxide (9.1 cc) while cooling in an ice bath. The mixture was stirred for 1.5 hours, and then water was added thereto. The precipitate was collected by filtration, washed with water and dried to yield crystals (33.2 g.) of 2,2,2-trichloroethyl 6-(2-phenylacetamido)-2,2-dimethylpenam-3-carboxylate-1-oxide, m.p. 165.5°–168.5° C.

EXAMPLE 2

2,2,2-trichloroethyl 6-(2-phenylacetamido)-2,2-dimethylpenam-3-carboxylate (466 mg.) was added to acetic acid (2 cc), and sodium percarbonate (377 mg.) was added thereto while cooling in an ice bath. The mixture was stirred for 30 minutes, and sodium tungstate dihydrate (40 mg.), acetic acid (1 cc) and water (1 cc) were added thereto. The mixture was stirred for 3 hours, and then water (50 cc) was added thereto. The precipitate was collected by filtration, washed with water and dried to yield crude crystals (400 mg.) of 2,2,2-trichloroethyl 6-(2-phenylacetamido)-2,2-dimethylpenam-3-carboxylate-1-oxide, m.p. 165°–167° C.

EXAMPLE 3

Vanadium pentoxide (22 mg.) was added to a solution of 2,2,2-trichloroethyl 6-(2-phenylacetamido)-2,2-dimethylpenam-3-carboxylate (466 mg.) in acetic acid (2 cc.), and 30% hydrogen peroxide (0.12 cc) was added dropwise, thereto while cooling in an ice bath. The mixture was stirred for 16 hours at the same temperature, and then water was added thereto. The mixture was extracted with ethyl acetate, and the ethyl acetate layer was washed with an aqueous solution of sodium bicarbonate and water, respectively, and dried. The solvent was distilled off to yield crude crystals (440 mg.) of 2,2,2-trichloroethyl 6-(2-phenylacetamide)-2,2-dimethylpenam-3-carboxylate-1-oxide.

EXAMPLE 4

Potassium 6-(2-phenylacetamido)-2,2-dimethylpenam-3-carboxylate (32.7 g.) was added to water (200 cc), and sodium tungstate dihydrate (1.2 g.) was added thereto. To this mixture was further added, dropwise, 30% hydrogen peroxide (12 cc) while cooling in an ice bath, and the mixture was stirred for 1.5 hours at the same temperature. The mixture was acidified to a pH 3 with 10% hydrochloric acid and extracted with ethyl acetate. The ethyl acetate layer was washed with water, dried, and then concentrated to yield a residue, crude crystals (33 g.) of 6-(2-phenylacetamido)-2,2-dimethylpenam-3-carboxylic acid-1-oxide. The crude crystals were recrystallized from a mixed solvent of ethyl acetate and n-hexane to yield pure crystals of m.p. 143°–145° C.

EXAMPLE 5

Acetic acid (10 cc) and water (2 cc) were added to potassium 6-(2-phenylacetamido)-2,2-dimethylpenam-3-carboxylate (1.86 g.), and sodium tungstate dihydrate (120 mg.) and sodium percarbonate (1.85 g.) were added thereto. The mixture was stirred for 2 hours, acidified at pH 3 with water (50 cc) and 10% hydrochloric acid, and extracted with ethyl acetate. The ethyl acetate layer was washed with water, dried and concentrated to give, as the residue, crude crystals (1.38 g.) of 6-(2-phenylacetamido)-2,2-dimethylpenam-3-carboxylic acid-1-oxide.

EXAMPLE 6

Acetic acid (10 cc) was added to 6-(2-phenoxyacetamido)-2,2-dimethylpenam-3-carboxylic acid (3.50 g.), and sodium tungstate dihydrate (100 mg.) was further added thereto. To the mixture was added 30% hydrogen peroxide (1.2 cc) while cooling in an ice bath, and the mixture was stirred for 1 hour. Water was added to the mixture and the precipitate was collected by filtration, washed with water and dried to yield crystals (3.24 g.) of 6-(2-phenoxyacetamido)-2,2-dimethylpenam-3-carboxylc acid-1-oxide, m.p. 166°–167° C.

EXAMPLE 7

Acetic acid (10 cc) was added to 6-(2-phenoxyacetamido)-2,2-dimethylpenam-3-carboxylic acid (1.75 g.), and sodium percarbonate (1.89 g.) was added thereto at 10°–15° C. To the mixture were added water (2 cc) and sodium tungstate dihydrate (120 mg.), and the mixture was stirred for 2 hours. The mixture was acidified to a pH 3 with water (50 cc) and 10% hydrochloric acid. The precipitate was collected by filtration, washed with water and dried to yield crude crystals (1.31 g.) of 6-(2-phenoxyacetamido)-2,2-dimethylpenam-3-carboxylic acid-1-oxide, m.p. 160°–161° C.

EXAMPLE 8

6-amino-2,2-dimethylpenam-3-carboxylic acid (1.06 g.) was suspended in water (6 cc), and sodium tungstate dihydrate (10 mg.) was added thereto. To the stirred mixture was added, dropwise, 30% hydrogen peroxide (0.8 cc) while cooling in an ice bath over a period of 20 minutes, and the mixture was stirred for 1 hour at the same temperature. To this mixture was added, dropwise, cooled acetonitrile (90 cc), and the precipitate was collected by filtration and dried under reduced pressure to yield a pale yellowish powder (0.85 g.) of 6-amino-2,2-dimethylpenam-3-carboxylic acid-1-oxide.

Analysis: $C_8H_{12}N_4O_4S.\frac{1}{2} H_2O$: Calculated: C 39.83, H 5.22, N 11.61; Found: C 40.03, H 5.33, N 11.81.

EXAMPLE 9

6-phenylglycylamino-2,2-dimethylpenam-3-carboxylic acid (1.87 g.; purity 89%) was suspended in water (8 cc), and sodium tungstate dihydrate (0.01 g.) was added thereto. To the stirred mixture was added, dropwise, hydrogen peroxide (0.9 cc) while cooling in an ice bath over 20 minutes, and the mixture was stirred for 2 hours at the same temperature. To the mixture was added its 10-fold volume of acetonitrile and the mixture was allowed to stand overnight. The precipitate was collected by filtration, and dried to yield a colorless powder (1.3 g.) of 6-phenylglycylamino-2,2-dimethylpenam-3-carboxylic acid-1-oxide.

Infrared spectrum (Nujol): 1780, 1688, 1600 cm$^{-1}$

EXAMPLE 10

6-(2-phenoxyacetamido)-2,2-dimethylpenam-3-carboxylic acid (1.0 g.) was suspended in glacial acetic acid (3 cc) and sodium molybdate (0.01 g.) was added thereto. To the stirred mixture was added, dropwise, 30% hydrogen peroxide (0.7 cc) while cooling in an ice bath over a period of 5 minutes. One hour later, the precipitate was collected by filtration, washed with water and dried to yield colorless crystals (0.85 g.) of 6-(2-phenoxyacetamido)-2,2-dimethylpenam-3-carboxylic acid-1-oxide, m.p. 166.5° C.

EXAMPLE 11

1-cyclopropylethyl 6-(2-phenylacetamido)-2,2-dimethylpenam-3-carboxylate (1.55 g.) was dissolved in acetic acid (8 cc) and sodium tungstate (10 mg.) was added thereto. To the stirred mixture was added, dropwise, 30% hydrogen peroxide (0.53 g.) while cooling in an ice bath and the mixture was stirred for a period of 30 minutes at this temperature. Water was added to the mixture and the aqueous solution was extracted with ethyl acetate. The ethyl acetate layer was washed in turn with a saturated aqueous solution of sodium bicarbonate, water, and a saturated aqueous solution of sodium chloride, dried and concentrated. The residue was dissolved in ether and the ether solution was allowed to stand. The precipitate was collected by filtration to yield crystals (1.53 g.) of 1-cyclopropylethyl 6-(2-phenylacetamido)-2,2-dimethylpenam-3-carboxylate-1-oxide, m.p. 158°–159° C.

The following compounds were obtained according to a manner similar to those of the above Examples:

(a) 2,2,2-trichloroethyl 6-[N-(1-cyclopropylethoxycarbonyl)phenylglycyl]amino-2,2-dimethylpenam-3-carboxylate-1-oxide, m.p. 166°–168° C.
(b) 2,2,2-trichloroethyl 6-[N-(2,2,2-trichloroethoxycarbonyl)phenylglycyl]amino-2,2-dimethylpenam-3-carboxylate-1-oxide, m.p. 178°–180° C.
(c) 2,2,2-trichloroethyl 6-(2-acetoxy-2-phenylacetamido)-2,2-dimethylpenam-3-carboxylate-1-oxide, m.p. 178°–180° C.
(d) 2,2,2-trichloroethyl 6-[2-(1H-tetrazole-1-yl)-acetamido]-2,2-dimethylpenam-3-carboxylate-1-oxide, m.p. 153°–154° C.
(e) Methyl 6-[N-(2,2,2-trichloroethoxycarbonyl)phenylglycyl]amino-2,2-dimethylpenam-3-carboxylate-1-oxide, m.p. 155°–158° C.
(f) 2,2,2-trichloroethyl 6-(2-cyanoacetamido)-2,2-dimethylpenam-3-carboxylate-1-oxide, m.p. 171°–172° C. (dec.).
(g) 2,2,2-trichloroethyl 6-[2-(thiophene-2-yl)-acetamido]-2,2-dimethylpenam-3-carboxylate-1-oxide, m.p. 167.5°–168.5° C.
(h) 2,2,2-trichloroethyl 6-[2-(sydnon-3-yl)acetamido]-2,2-dimethylpenam-3-carboxylate-1-oxide, m.p. 141°–142° C. (dec.).
(i) Methyl 6-(2-phenylacetamido)-2,2-dimethylpenam-3-carboxylate-1-oxide, m.p. 126.5°–127.5° C.
(j) 2,2,2-trichloroethyl 6-[2-(p-hydroxyphenyl)-2-(1-cyclopropylethoxy)carbonylaminoacetamido]-2,2-dimethylpenam-3-carboxylate-1-oxide, m.p. 145° C.

Reaction of:

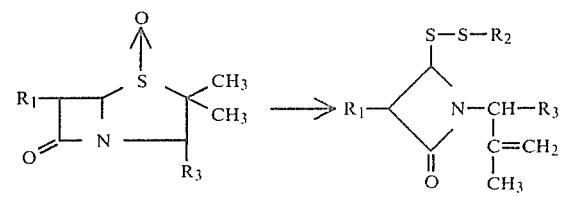

EXAMPLE 1

A mixture of methyl 6-(2-phenoxyacetamido)-2,2-dimethylpenam-3-carboxylate-1-oxide (3.80 g.) and 5-methyl-1,3,4-thiadiazole-2-thiol (1.32 g.) in t-butanol (50 cc) was refluxed for 24 hours. The reaction mixture was concentrated to dryness under reduced pressure and the residue was dissolved in ethyl acetate (100 cc). The solution was washed with 5% aqueous sodim carbonate solution three times and then water, dried over magnesium sulfate and concentrated to give a residue (4.41 g.). The residue was subjected to chromatography on silica gel to yield powders of methyl 4-(5-methyl-1,3,4-thiadiazole-2-yl)dithio-3-(2-phenoxyacetamido)-α-isopropenyl-2-oxoazetidine-1-acetate.

Infrared spectrum (chloroform): 3430, 1779, 1742, 1692 cm$^{-1}$

EXAMPLE 2

A mixture of 6-(2-phenoxyacetamido)-2,2-dimethylpenam-3-carboxylic acid-1-oxide (2.18 g.) and 5-methyl-1,3,4-thiadiazole-2-thiol (1.00 g.) in t-butanol (100 cc) was heated under reflux for 25 hours. The reaction mixture was concentrated to dryness under reduced pressure and ethyl acetate was added to the residue. Crystals were separated out and collected by filtration and recrystallized from ethyl acetate to yield crystals (1.60 g.) of 4-(5-methyl-1,3,4-thiadiazole-2-yl)dithio-3-(2-phenoxyacetamido)-α-isopropenyl-2-oxoazetidine-1-acetic acid, m.p. 142°–144° C.

EXAMPLE 3

A mixture of methyl 6-(2-phenoxyacetamido)-2,2-dimethylpenam-3-carboxylate-1-oxide (3.80 g.) and benzothiazole-2-thiol (1.67 g.) in methylisobutylketone (25 cc) was heated under reflux for 80 minutes. The reaction mixture was concentrated to dryness under reduced pressure and the residue was dissolved in ethyl acetate (20 cc) under warming. After cooling, the crystals were separated out and were collected by filtration, and the filtrate was washed with 5% aqueous sodium carbonate and water, dried and then concentrated. The precipitate was combined with the crystals obtained before and recrystallized from ethyl acetate to yield crystals (3.92 g.) of methyl 4-(benzothiazole-2-yl)dithio- 3-(2-phenoxyacetamido)-α-isopropenyl-2-oxoazetidine-1-acetate, m.p. 146°–147° C.

EXAMPLE 4

A mixture of methyl 6-(2-phenoxyacetamido)-2,2-dimethylpenam-3-carboxylate-1-oxide (0.18 g.) and benzothiazole-2-thiol (0.08 g.) in toluene (4 cc) was heated under reflux for 4 hours. The reaction mixture was allowed to stand, and crystals were separated out and collected by filtration. The filtrate was concentrated to dryness, and the residue was dissolved in ethyl acetate (3 cc) under warming. The filtrate was allowed to stand, and crystals were separated out and were collected by filtration, combined with the crystals obtained before to yield crystals (186 mg.) of methyl 4-(benzothiazole-2-yl)dithio-3-(2-phenoxyacetamido)-α-isopropenyl-2-oxoazetidine-1-acetate, m.p. 146°–147° C.

EXAMPLE 5

A mixture of methyl 6-(2-phenoxyacetamido)-2,2-dimethylpenam-3-carboxylate-1-oxide (0.180 g.) and benzothiazole-2-thiol (0.084 g.) in benzene (4 cc) was heated under reflux for 19 hours. The reaction mixture was treated in a similar manner to that of Example 4 to yield crystals (185 mg.) of methyl 4-(benzothiazole-2-yl)dithio-3-(2-phenoxyacetamido)-α-isopropenyl-2-oxoazetidine-1-acetate, m.p. 146°–147° C.

EXAMPLE 6

A mixture of 6-(2-phenoxyacetamido)-2,2-dimethylpenam-3-carboxylic acid-1-oxide (10.9 g.) and benzothiazole-2-thiol (5.01 g.) in t-butanol (500 cc) was heated under reflux for 20 hours. The reaction mixture was concentrated to dryness under reduced pressure and the residue was washed with ether to yield crystals (11.95 g.) of 4-(benzothiazole-2-yl)dithio-3-(2-phenoxyacetamido)-α-isopropenyl-2-oxoazetidine-1-acetic acid, m.p. 146°–148° C.

EXAMPLE 7

A mixture of methyl 6-(2-phenoxyacetamido)-2,2-dimethylpenam-3-carboxylate-1-oxide (1.14 g.) and benzylthiol (620 mg.) in methylisobutylketone (20 cc) was heated under reflux for 15 hours. The reaction mixture was concentrated under reduced pressure, and the residue was dissolved in ether, and then petroleum ether was added thereto. The oily layer was separated by decantation, and subjected to chromatography on silica gel and eluated with chloroform. The eluate was concentrated to yield an oil (180 mg.) of methyl 4-benzyldithio-3-(2-phenoxyacetamido)-α-isopropenyl-2-oxoazetidine-1-acetate.

Infrared spectrum (Chloroform): 3400, 1780, 1750, 1697 cm$^{-1}$

EXAMPLE 8

A mixture of 2,2,2-trichloroethyl 6-(2-phenylacetamido)-2,2-dimethylpenam-3-carboxylate-1-oxide (0.48 g.) and benzothiazole-2-thiol (0.17 g.) in dry toluene (15 cc) was heated under reflux for 5 hours. The reaction mixture was concentrated under reduced pressure and ether was added to the residue. Crystals were separated out and collected by filtration, washed with ether and recrystallized from acetonitrile to yield crystals (0.57 g.) of 2,2,2-trichloroethyl 4-(benzothiazole-2-yl)dithio-3-(2-phenylacetamido) α-isopropenyl-2-oxoazetidine-1-acetate, m.p. 140°–141° C.

EXAMPLE 9

A mixture of methyl 6-(2-phenoxyacetamido)-2,2-dimethylpenam-3-carboxylate-1-oxide (0.38 g.) and thioacetic acid (0.08 g.) in dry benzene (7.5 cc) was heated under reflux for 18 hours. The reaction mixture was concentrated, and the residue was subjected to chromatography on silica gel and eluated with chloroform. The solvent was distilled off from the eluate to yield an oil (0.15 g.) of methyl 4-acetyldithio-3-(2-phenoxyacetamido)-α-isopropenyl-2-oxoazetidine-1-acetate.

Infrared spectrum: 1780, 1745, 1690 cm$^{-1}$

EXAMPLE 10

A mixture of methyl 6-(2-phenoxyacetamido)-2,2-dimethylpenam-3-carboxylate-1-oxide (1.84 g.) and thiophenol (0.552 g.) in benzene (80 cc) was heated under reflux for 30 hours. The reaction mixture was concentrated under reduced pressure and the residue was dissolved in chloroform. The solution was washed with 5% aqueous sodium carbonate solution three times and water, dried and concentrated. The residue was subjected to chromatography on silica gel and eluated with a mixture (300 cc) of ether and petroleum ether (1:3) and then with ether. Each 50 cc of the eluate was separately taken as fractions, and the fifth fraction was concentrated to yield a colorless oil (0.58 g.) of methyl 4-phenyldithio-3-(2-phenoxyacetamido)-α-isopropenyl-2-oxoazetidine-1-acetate.

Infrared spectrum (liquid film): 1780, 1747, 1690 cm$^{-1}$

EXAMPLE 11

A mixture of methyl 6-(2-phenoxyacetamido)-2,2-dimethylpenam-3-carboxylate-1-oxide (0.368 g.), thiazole-2-thiol (117 mg.) and t-butanol (15 cc) was heated under reflux for 30 hours. The reaction mixture was concentrated, and the residue was subjected to chromatography on silica gel and eluated with chloroform. Each 50 cc. of the eluate was separately taken as fractions, and the first and second fractions were concentrated to yield a colorless oil (0.405 g.) of methyl-4-(thiazole-2-yl)dithio-3-(2-phenoxyacetamido)-α-isopropenyl-2-oxoazetidine-1-acetate.

Infrared spectrum (Liquid film): 1780, 1747, 1687 cm$^{-1}$

EXAMPLE 12

A mixture of methyl 6-(2-phenoxyacetamido)-2,2-dimethylpenam-3-carboxylate-1-oxide (0.736 g.), benzoxazole-2-thiol (0.302 g.) and benzene (20 cc) was heated under reflux for 19 hours. The reaction mixture was treated in a similar manner to that of Example 11 and the sixth fraction was concentrated to yield a colorless oil of methyl 4-(benzoxazole-2-yl)dithio-3-(2-phenoxyacetamido)-α-isopropenyl-2-oxoazetidine-1-acetate.

Infrared spectrum (Liquid film): 1780, 1742, 1685 cm$^{-1}$

EXAMPLE 13

A mixture of methyl 6-(2-phenoxyacetamido)-2,2-dimethylpenam-3-carboxylate-1-oxide (0.368 g.), quinoline-2-thiol (0.161 g.) and methylisobutyl-ketone (10 cc) was heated under reflux for 6 hours. The reaction mixture was concentrated under reduced pressure, and the residue was subjected to chromatography on silica gel and eluated with chloroform. Each 50 cc of the eluate was separately taken as fractions, and the eighth and ninth fractions were concentrated. The residue was subjected to chromatography on silica gel and eluated with chloroform. Each 30 cc of the eluate was separately taken as fractions. The eighth fraction was concentrated to yield an oil of methyl 4-(quinoline-2-yl)dithio-3-(2-phenoxyacetamido)-α-isopropenyl-2-oxazetidine-1-acetate.

Infrared spectrum (Nujol): 1775, 1745, 1685 cm$^{-1}$

EXAMPLE 14

A mixture of 2,2,2-trichloroethyl 6-(2-phenoxyacetamido)-2,2-dimethylpenam-3-carboxylate-1-oxide (497 mg.), benzothiazole-2-thiol (167 mg.) and toluene (10 cc) was heated under reflux for 4 hours. After cooling, the crystals were separated out and collected by filtration, the filtrate was concentrated, and the residue was washed with ethyl acetate and then combined with the crystals obtained before. The thus combined substances (total 500 mg.) were recrystallized from ethyl acetate to yield crystals of 2,2,2-trichloroethyl 4-(benzothiazole-2-yl)dithio-3-(2-phenoxyacetamido)-α-isopropenyl-2-oxoazetidine-1-acetate, m.p. 171°–174.5° C.

EXAMPLE 15

A mixture of 2,2,2-trichloroethyl 6-[N-(2,2,2-trichloroethoxycarbonyl)phenylglycyl]amino-2,2-dimethylpenam-3-carboxylate-1-oxide (500 mg.), benzothiazole-2-thiol(125 mg.) and toluene (20 cc) was heated under reflux for 3 hours. The reaction mixture was concentrated under reduced pressure and the residue was refined according to a conventional manner to yield 2,2,2-trichloroethyl 4-(benzothiazole-2-yl)dithio-3-[N-(2,2,2-trichloroethoxycarbonyl)phenylglycyl]amino]-α-isopropenyl-2-oxoazetidine-1-acetate.

Analysis for $C_{28}H_{24}N_4O_6S_3Cl_6$: Calculated: C 40.94, H 2.94, N 6.84, Cl 25.89; Found: C 40.91, H 2.76, N 6.67, Cl 26.01

EXAMPLE 16

A mixture of methyl 6-(2-phenoxyacetamido)-2,2-dimethylpenam-3-carboxylate-1-oxide (0.736 g.), benzoxazole-2-thiol (0.604 g.) and toluene (20 cc) was heated under reflux for 7 hours. The reaction mixture was concentrated to yield an oily residue (1.25 g.) of methyl 3-(2-phenoxyacetamido)-4-(benzoxazole-2-yl)dithio-α-isopropenyl-2-oxoazetidine-1-acetate.

This substance was identified with the preparation of Example 12 by Infrared spectrum.

EXAMPLE 17

A mixture of methyl 6-(2-phenoxyacetamido)-2,2-dimethylpenam-3-carboxylate-1-oxide (0.736 g.), benzoxazole-2-thiol (0.604 g.) and methylisopropylketone (20 cc) was heated under reflux for 5 hours. The reaction mixture was concentrated under reduced pressure and the residue was decolorized with activated carbon to give an oil (1.19 g.) of methyl 3-(2-phenoxyacetamido)-4-(benzoxazole-2-yl)dithio-α-isopropenyl-2-oxoazetidine-1-acetate.

EXAMPLE 18

A mixture of acetoxime ester (1.69 g.) of 6-(2-phenoxyacetamido)-2,2-dimethylpenam-3-carboxylic acid-1-oxide, benzothiazole-2-thiol (0.67 g.) and toluene (30 cc) were heated under reflux for 5 hours. The reaction mixture was treated with activated carbon, dried over magnesium sulfate and concentrated. The residue was subjected to chromatography on silica gel to yield an oil (1.25 g.) of acetoxime ester of 4-(benzothiazole-2-yl)dithio-3-(2-phenoxyacetamido)-α-isopropenyl-2-oxoazetidine-1-acetic acid.

Infrared spectrum (Chloroform): 3430, 1780, 1695 cm$^{-1}$

EXAMPLE 19

A mixture of 2,2,2-trichloroethyl 6-(2-phenylacetamido)-2,3-dimethylpenam-3-carboxylate-1-oxide (2.41 g.), 5-methyl-1,3,4-thiadiazole-2-thiol (0.66 g.) and toluene (30 cc) was heated under reflux for 3.5 hours. The toluene was distilled off and the residue was subjected to chromatography on silica gel and eluated with chloroform. The eluate was concentrated and the residual oil was crystallized from ether. The crystals were recrystallized from ether to yield crystals (1.80 g.) of 2,2,2-trichloroethyl 4-(5-methyl-1,3,4-thiadiazole-2-yl)-dithio-3-(2-phenylacetamido)-α-isopropenyl-2-oxoazetidine-1-acetate, m.p. 108°–109° C.

EXAMPLE 20

6-(2-phenylacetamido)-2,2-dimethylpenam-3-carboxylic acid-1-oxide (1.0 g.), benzothiazole-2-thiol (480 mg.) and t-butanol (50 cc) was heated under reflux for 24 hours. The solvent was distilled off under reduced pressure and the residue was washed with diisopropylether to yield a faint reddish powder (1.85 g.) of 4-(2-benzothiazole-2-yl)dithio-3-(2-phenylacetamido)-α-isopropentyl-2-oxoazetidine-1-acetic acid, m.p. 76°–80° C.

EXAMPLE 21

Amorphism of 2,2,2-trichloroethyl 4-(benzothiazole-2-yl)dithio-3-[N-(t-butoxycarbonyl)phenylglycyl]amino-α-isopropenyl-2-oxoazetidine-1-acetate was obtained in a similar method as that of Example 15 by using 2,2,2-trichloroethyl 6-[N-(t-butoxycarbonyl)-phenylglycyl]amino-2,2-dimethylpenam-3-carboxylate-1-oxide instead of 2,2,2-trichloroethyl 6-[N-(2,2,2-trichloroethoxycarbonyl)phenylglycyl]amino-2,2-dimethylpenam-3-carboxylate-1-oxide.

EXAMPLE 22

A mixture of 1-cyclopropylethyl 6-(2-phenylacetamido)-2,2-dimethylpenam-3-carboxylate-1-oxide (0.70 g.) and benzothiazole-2-thiol (0.28 g.) in toluene (14 cc) was located under reflux for 4 hours. After cooling the mixture was concentrated under reduced pressure and ether. was added to the residue, and precipitate was collected by filtration to yield crystals (0.59 g.) of 1-cyclopropylethyl 4-(benzothiazole-2-yl)dithio-3-(2-phenylacetamido)-α-isopropenyl-2-oxoazetidine-1-acetate, m.p. 114°–117° C.

EXAMPLE 23

A solution of 2,2,2-trichloroethyl 6-(2-phenylacetamido)-2,2-dimethylpenam-3-carboxylate-1-oxide (1.0 g.) and benzoxazole-2-thiol (0.32 g.) in tetrahydrofuran was heated at 120° C. for 6 hours. The reaction mixture was washed with 5% aqueous sodium bicarbonate solution and water, dried and then concentrated to yield an oil (1.1 g.) of 2,2,2-trichloroethyl 4-(benzoxazole-2-yl)dithio-3-(2-phenylacetamido)-α-isopropenyl-2-oxoazetidine-1-acetate.

Infrared spectrum: 3280, 1785, 1765, 1660 cm$^{-1}$

EXAMPLE 24

A mixture of 2,2,2-trichloroethyl 6-(1-ethoxycarbonyl-1-propene-2-yl)amino-2,2-dimethylpenam-3-carboxylate-1-oxide (0.95 g.), benzothiazole-2-thiol (0.34 g.) and toluene (10 cc) was heated under reflux for 3 hours. The toluene was distilled off and the residue was subjected to chromatography on silica gel and eluated with chloroform to yield an oil (0.49 g.) of 2,2,2-trichloroethyl 4-(benzothiazole-2-yl)dithio-3-(1-ethoxycarbonyl-1-propene-2-yl)amino-α-isopropenyl-2-oxoazetidine-1-acetate.

Infrared spectrum (Liquid film): 3250, 1770, 1655 cm$^{-1}$

EXAMPLE 25

2,2,2-trichloroethyl 6-[2-(thiophene-2yl)acetamido]-2,2-dimethylpenam-3-carboxylate-1-oxide (4.39 g.) and benzothiazole-2-thiol (1.51 g.) were dissolved in toluene (44 cc), and the mixture was refluxed for 2 hours. The mixture was dried while it was still hot and allowed to stand. The precipitate was collected by filtration and the filtrate was concentrated. The precipitate in the residue was collected by filtration. Both precipitates were combined with each other and recrysallized from benzene to yield crystals (3.50 g.) of 2,2,2-trichloroethyl 4-(benzothiazole-2-yl)dithio-3-[2-(thiophene-2-yl)acetamido]-α-isopropenyl-2-oxoazetidine-1-acetate, m.p. 136°–137° C.

EXAMPLE 26

A mixture of 4-hydroxy-3,5-di(tert)butylbenzyl 6-(2-phenylacetamido)-2,2-dimethylpenam-3-carboxylate-1-oxide (0.73 g.), benzothiazole-2-thiol (0.22 g.) and toluene (10 cc) was refluxed for 4 hours and then concentrated under reduced pressure. To the residue was added ether and the ether was allowed to stand. The precipitate was collected by filtration to yield crystals (0.67 g.) of 4-hydroxy-3,5-di(tert)butylbenzyl 4-(benzothiazole-2-yl)dithio-3-(2-phenylacetamido)-α-isopropenyl-2-oxoazetidine-1-acetate.

Infrared spectrum: 1785, 1748, 1650 cm$^{-1}$

The following compounds were obtained in a similar manner to that of the above Examples:

(a) 2,2,2-trichloroethyl 4-(benzothiazole-2-yl)dithio-3-[2-(sydonone-3-yl)acetamido]-α-isopropenyl-2-oxoazetidine-1-acetate.

Infrared spectrum (Nujol): 3250, 1780, 1735, 1650 cm$^{-1}$ (b) 2,2,2-trichloroethyl 4-(benzothiazole-2-yl)dithio-3-[N-(1-cyclopropylethoxycarbonyl)phenylglycyl]amino-α-isopropenyl-2-oxoazetidine-1-acetate, m.p. 164°–165° C.

(c) 2,2,2-trichloroethyl 4-(benzothiazole-2-yl)dithio-3-(2-cyanoacetamido)-α-isopropenyl-2-oxoazetidine-1-acetate, m.p. 117°–119° C.

(d) 2,2,2-trichloroethyl 4-(benzothiazole-2-yl)dithio-3-[2-(p-hydroxyphenyl)-2-(1-cyclopropylethoxy)carbonylaminoacetamido]-α-isopropenyl-2-oxoazetidine-1-acetate, m.p. 175°–176° C.

Reaction of:

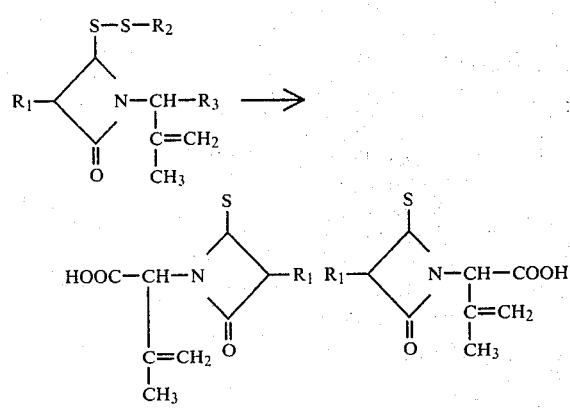

EXAMPLE 1

4-(benzothiazole-2-yl)dithio-3-(2-phenoxyacetamido)-α-isopropenyl-2-oxoazetidine-1-acetic acid (1.0 g.) was dissolved in water containing sodium bicarbonate (126 mg.) at 30° C. The mixture was stirred for 30 minutes and the precipitate was separated out by filtration. The filtrate was acidified by a 10% phosphoric acid aqueous solution of a pH of 2 and extracted with ethyl acetate. The ethyl acetate layer was dried over magenesium sulfate and concentrated to yield as a residue, crystals (620 mg.) of 4,4′-dithio-bis[3-(2-phenoxyacetamido)-α-isopropenyl-2-oxoazetidine-1-acetic acid], m.p. 189°–190° C. (dec.).

Reaction of:

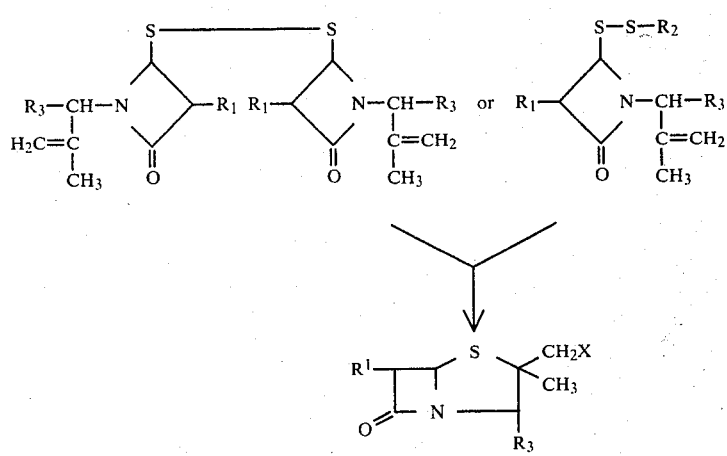

EXAMPLE 1

2,2,2-trichloroethyl 4-(benzothiazole-2-yl)dithio-3-(2-phenylacetamido)-α-isoprenyl-2-oxoazetidine-1-acetate (1.20 g.) was dissolved in chloroform (20 cc), and to the stirred solution was added acetamide (0.36 g.) while cooling in an ice bath. A carbon tetrachloride solution (1.92 g.) which contains 10 w/w% bromine was added, dropwise, to the solution and the mixture was stirred for 1 hour. The precipitate was separated out by filtration and the filtrate was washed with water, dried and concentrated. The residue was dissolved in ether and the ethereal solution was filtered and then concentrated. The precipitate was collected by filtration and recrystallized from ether to yield crystals (0.89 g.) of 2,2,2-trichloroethyl 6-(2-phenylacetamido)-2-methyl-2-bromomethylpenam-3-carboxylate, m.p. 90°–93° C.

Infrared spectrum (Nujol): 3320, 1790, 1767, 1658 cm$^{-1}$

EXAMPLE 2

4-(benzothiazole-2-yl)dithio-3-(2-phenoxyacetamido)-α-isopropenyl-2-oxoazetidine-1-acetic acid (2.06 g.) was dissolved in tetrahydrofuran (20 cc), and to the stirred solution was added, dropwise, a carbon tetrachloride solution (3.2 g.) which contains 10 w/w% bromine. The reaction mixture was stirred for 1 hour and then the precipitate was separated out by filtration. The filtrate was concentrated under reduced pressure and to the residue was added a small amount of ethyl acetate. The ethyl acetate solution was washed with a saturated aqueous solution of sodium chloride, dried and concentrated. To the residue was added a small amount of ethyl acetate, and then the precipitate was collected by filtration to yield crystals (1.6 g.) of 6-(2-phenoxyacetamido)-2-methyl-2-bromomethylpenam-3-carboxylic acid, m.p. 164.5°–165.5° C.

Infrared spectrum (Nujol): 1790, 1745, 1650 cm$^{-1}$

EXAMPLE 3

4-(5-methyl-1,3,4-thiadiazole-2-yl)dithio-3-(2-phenoxyacetamido)-α-isopropenyl-2-oxoazetidine-1-acetic acid was reacted in a manner similar to that of Example 2 to yield crystals of 6-(2-phenoxyacetamido)-2-methyl-2-bromomethylpenam-3-carboxylic acid, m.p. 164.5°–165.5° C.

EXAMPLE 4

A mixture of 2,2,2-trichloroethyl 4-(benzothiazole-2-yl)dithio-3-[N-(2,2,2-trichloroethoxycarbonyl)phenylglycyl]amino-α-isopropenyl-2-oxoazetidine-1-acetate (2.0 g.), acetamide (0.408 g.) and absolute chloroform (37 cc) was cooled at below 4° C., and thereto was added, dropwise, a carbon tetrachloride solution (3.93 g.) which contains 10 2/2 w/w bromine. The reaction mixture was stirred for 15 minutes at the same temperature and filtered. The filtrate was washed with a saturated aqueous solution of sodium chloride and then with water, dried and then conentrated. The residue was dissolved in ethyl acetate and the ethyl acetate solution was filtered. The filtrate was concentrated to yield, as the residue, powder (1.7 g.) of 2,2,2-trichloroethyl 6-[N-(2,2,2-trichloroethoxycarbonyl)phenylglycyl]amino-2-methyl-2-bromomethylpenam-3-carboxylate.

Infrared spectrum (Nujol): 1788, 1760, 1735, 1687 cm$^{-1}$

EXAMPLE 5

To a stirred mixture of 2,2,2-trichloroethyl 4-(benzothiazole-2-yl)dithio-3-(2-phenoxyacetamido)-α-isopropenyl-2-oxoazetidine-1-acetate (647 mg.), acetamide (150 mg.) and chloroform (10 cc) was added while cooling in an ice bath, a carbon tetrachloride solution (960 mg.) which contains 10 w/w% bromine. The reaction mixture was stirred for 1 hour at the same temperature and then for 30 minutes at 15° C., and filtered. The filtrate was washed with a saturated aqueous solution of sodium chloride and then with water, dried and concentrated. To the residue was added ether and the ethereal solution was filtered. The solvent of the filtrate was distilled off to yield a viscous oil (500 mg.) of 2,2,2-trichloroethyl 6-(2-phenoxyacetamido)-2-methyl-2-bromomethylpenam-3-carboxylate.

Infrared spectrum (Chloroform): 3430, 1792, 1768, 1692 cm$^{-1}$

EXAMPLE 6

A carbon tetrachloride solution (800 mg.) which contains 10 w/w% bromine was added dropwise while cooling in an ice bath to a stirred solution of methyl 4-(benzothiazole-2-yl)dithio-3-(2-phenoxyacetamido)-α-isopropenyl-2-oxoazetidine-1-acetate (530 mg.) and acetamide (120 mg.) in tetrahydrofuran (5 cc). The mixture was filtered and the filtrate was concentrated under reduced pressure. The residue was dissolved in ethyl acetate and the solution was washed in turn with water, an aqueous solution of sodium carbonate and water. The solution was dried and concentrated to yield, as the residue, an oil (430 mg.) of methyl 6-(2-phenoxyacetamido)-2-methyl-2-bromomethylpenam-3-carboxylate.

Infrared spectrum (CDCl$_3$): 3350, 1785, 1748, 1690 cm$^{-1}$

EXAMPLE 7

2,2,2-trichloroethyl 4-(benzothiazole-2-yl)dithio-3-(2-phenylacetamido)-α-isopropenyl-2-oxoazetidine-1-acetate (2.0 g.) was dissolved in absolute chloroform (40 cc), and to the solution was added dropwise a 2° C. a solution of o-nitrobenzenesulfenylchloride (0.9 g.) in absolute chloroform (20 cc). The reaction temperature was gradually elevated up to 20°–25° C. during 1 hour, and then the mixture was stirred for 6 hours at this temperature. The mixture was concentrated under reduced pressure and the residue was recrystallized from ether to yield crystals (1.24 g.) of 2,2,2-trichloroethyl 6(2-phenylacetamido)-2-methyl-2-chloromethylpenam-3-carboxylate, m.p. 104°–105° C.

Infrared spectrum (Nujol):
1785, 1763, 1656 cm$^{-1}$

EXAMPLE 8

2,2,2-trichloroethyl 4-(benzothiazole-2-yl)dithio-3(2-phenylacetamido)-α-isopropenyl-2-oxoazetidine-1-acetate (1.9 1 g.) was dissolved in dichloromethane (20 cc), and the solution was cooled at −25° C. Phosphorus pentachloride (1.0 g.) was added to the solution and the mixture was stirred for 3 hours and then poured into water (20 cc). The aqueous solution was neutralized by sodium bicarbonate, and the organic layer was washed with water, dried and concentrated. The residue was subjected to a chromatography of silica gel in which a mixed solvent of benzene and ethyl acetate (1:1) was used as eluant. The eluate was concentrated to yield, as the residue, crystals of 2,2,2-trichloroethyl 6-(2-phenylacetamido)-2-methyl-2-chloromethylpenam-3-carboxylate, m.p. 103°–105° C.

EXAMPLE 9

A carbon tetrachloride solution (7.0 g.) which contains 10 w/w% chlorine was added dropwise over 10 minutes to a mixture of 2,2,2-trichloroethyl 4-(benzothiazole-2-yl)dithio-3(2phenylacetamido)-α-isopropenyl-2-oxoazetidine-1-acetate (2.1 g.), acetamide (0.4 g.) and chloroform (20 cc) at room temperature. The mixture was stirred for 30 minutes at the same temperature and filtered. The filtrate was washed with a saturated aqueous solution of sodium bicarbonate and then with water, dried and then concentrated. The residue was dissolved in ethyl acetate (20 cc) and the solution was filtered. The filtrate was concentrated to dryness and to the residue was added diisopropylether. The precipitate was collected by filtration to yield a pale yellowish powder (1.2 g.) of 2,2,2-trichloroethyl 6-(2-phenylacetamido)-2-methyl-2-chloromethylpenam-3-carboxylate, m.p. 104°–105° C. (dec.).

EXAMPLE 10

2,2,2-trichloroethyl 4-(benzothiazole-2-yl)dithio-3-(2-phenylacetamido)-β-isopropenyl-2-oxoazetidine-1-acetate (1.0 g.) was dissolved in dichloroethane (15 cc) and to the solution was added acetamide (0.1 g.). A solution of sulfur dichloride (0.11 g.) in dichloroethane (3 cc) was added, dropwise, at −10° to −15° C. to the solution and the solution was stirred 30 minutes at this temperature. The solution was filtered and the filtrate was concentrated. The residue was recrystallized from ether to yield colorless crystals (0.71 g.) 2,2,2-trichloroethyl 6(2-phenylacetamido)-2-methyl-2-chloromethylpenam-3-carboxylate, m.p. 103°–105° C.

EXAMPLE 11

2,2,2-trichloroethyl 4-(benzothiazole-2-yl)dithio-3-(2-phenylacetamido)-α-isopropenyl-2-oxoazetidine-1-acetate (1.0 g.) was dissolved in acetamide (0.1 g.), and to the solution was added, dropwise, a solution of sulfur monochloride (0.17 g.) in dichloroethane (5 cc) at −10° to −15° C. The mixture was stirred for 80 minutes at this temperature, washed with water, dried and concentrated. The residue was crystallized out from ether and then the crystals were recrystallized from ether to yield colorless ones (480 mg.) of 2,2,2-trichloroethyl 6-(2-phenylacetamido)-2-methyl-2-chloromethylpenam-3-carboxylate, m.p. 103°–105° C.

EXAMPLE 12

A mixture of thionylchloride (0.64 g.) and methylene chloride (3 cc) was added dropwise at −10~−15° C. to a solution of 2,2,2-trichloroethyl 4-(benzothiazole-2-yl)dithio-3-(2-phenylacetamido)-α-isopropenyl-2-oxoazetidine-1-acetate (5.05 g.) and acetamide (0.5 g.) in absolute methylene chloride (25 cc), and the mixture was stirred at 0° C. for 3 hours. The mixture was filtered and the filtrate was washed in turn with water, an aqueous solution of sodium bicarbonate and water, dried and concentrated. The residue was crystallized out from a small amount of ether to yield crystals (2.41 g.) of 2,2,2-trichloroethyl 6(2-phenylacetamido)-2-methyl-2-chloromethylpenam-3-carboxylate, m.p. 102°–105° C.

EXAMPLE 13

1-cyclopropylethyl 4(benzothiazole-2-yl)dithio-3(2-phenylacetamido)-α-isopropenyl-2-oxoazetidine-1-acetate (0.76 g.) was dissolved in chloroform (15 cc) and acetamide (0.22 g.) was added to the solution. A carbon tetrachloride solution (2.4 g.) which contains 10 w/w% bromine was added dropwise to the stirred solution under cooling, and then the mixture was stirred for 15 minutes. The mixture was filtered and the filtrate was washed with a saturated aqueous solution of sodium bicarbonate and then with water, dried and concentrated. The residue was dissolved in ethyl acetate and the solution was filtered and concentrated to yield, as the residue, an oil (0.76 g.) of 1-cyclopropylethyl 6-(2-phenylacetamido)-2-methyl-2-bromomethylpenam-3-carboxylate.

Infrared spectrum (Liquid film):
3500, 1780, 1730, 1660 cm$^{-1}$

EXAMPLE 14

Methyl 6-(2-phenoxyacetamido)-2-methyl-2-bromomethylpenam-3-carboxylate which was the same end product as that of Example 6 was obtained according to a similar manner to that of Example 6 in which each of the following compounds instead of methyl 4-(benzothiazole-2-yl)dithio-3-(2-phenoxyacetamido)-α-isopropenyl-2-oxoazetidine-1-acetate was used as the starting compound.
(a) Methyl 4-(5-methyl-1,3,4-thiadiazole-2-yl)dithio-3(2-phenoxyacetamido)-α-isopropenyl-2-oxoazetidine-1-acetate;
(b) Methyl 4-benzyldithio-3-(2-phenoxyacetamido)-α-isopropenyl-2-oxoazetidine-1-acetate;
(c) Methyl 4-phenyldithio-3-(2-phenoxyacetamido)-α-isopropenyl-2-oxoazetidine-1-acetate;
(d) Methyl 4-(thiazole-2-yl)dithio-3-(2-phenoxyacetamido)-α-isopropenyl-2-oxoazetidine-1-acetate;
(e) Methyl 4(benzoxazole-2-yl)dithio-3-(2-phenoxyacetamido)-α-isopropenyl-2-oxoazetidine-1-acetate;
(f) Methyl 4-(quinoline-2-yl)dithio-3-(2-phenoxyacetamido)-α-ispropenyl-2-oxoazetidine-1-acetate.

EXAMPLE 15

2,2,2-trichloroethyl 4-(benzothiazole-2-yl)dithio-3-[2-(thiophene-2-yl)acetamido]-α-isopropenyl-2-oxoazetidine-1-acetate (0.96 g.) was dissolved in methylene chloride (15 cc), and acetamide (0.09 g.) was added thereto. To the stirred mixture was added a carbon tetrachloride solution which contains 10 w/w% bromine while cooling in an ice bath. The mixture was stirred at this temperature for 1 hour and the precipitate was separated out by filtration. The filtrate was washed with a saturated sodium bicarbonate aqueous solution and then with water, dried over magnesium salts and evaporated to yield, as the residue, an oil (0.85 g.) of 2,2,2-trichloroethyl 6-[2-(thiophene-2-yl)acetamido]-2-methyl-2-bromomethylpenam-3-carboxylate.

Infrared spectrum (Liquid film): 3250, 1780, 1760, 1655 cm$^{-1}$

EXAMPLE 16

A carbon tetrachloride solution (0.202 g.) which contains 10 w/w% bromine was added dropwise to a solution of 4-hydroxy-3,5-di(tert)butylbenzyl 4-(benzothiazole-2-yl)dithio-3-(2-phenylacetamido)-α-isopropenyl-2-oxoazetidine-1-acetate (0.164 g.) and acetamide (0.0135 g.) in methylene chloride (10 cc) while cooling in an ice bath. The mixture was stirred for 1 hour at the same temperature, and the precipitate was separated out by filtration. The filrate was washed with a saturated aqueous solution of sodium bicarbonate and then with water, dried and concentrated. The residue was treated with absolute ether and the ether solution was filtered. The filtrate was concentrated and the residue was dried to yield colorless crystals (0.12 g.) of 4-hydroxy-3,5-di(-tert)butylbenzyl 6-(2-phenylacetamido)-2-methyl-2-bromomethylpenam-3-carboxylate.

Infrared spectrum: 1786, 1744, 1660 cm$^{-1}$

EXAMPLE 17

Pyridinium hydrobromide perbromide (320 mg.) was added to a mixture of 4,4'-dithio-bis[methyl-3-(2-phenoxyacetamido)-α-isopropenyl-2-oxoacetidine-1-acetate] (670 mg), pyridine (158 mg.) and 1,2-dimethoxyethane (10 cc). The mixture was stirred for 5 hours at room temperature and concentrated under reduced pressure. The residue was dissolved in ethyl acetate and the ethyl acetate layer was washed in turn with water, a dil. phosphoric acid aqueous solution, a sodium bicarbonate solution and water, dried and concentrated. The residue was subjected to a chromatography of silica gel in which chloroform was used as the eluant. The eluate was concentrated to yield, as the residue, an amorphous material (360 mg.) of methyl 7-(2-phenoxyacetamido)-3-methyl-3-bromocepham-4-carboxylate.

Infrared spectrum (Carbon tetrachloride): 3450, 1794, 1745, 1703 cm$^{-1}$

EXAMPLE 18

Methyl 4-(benzothiazole-2-yl)dithio-3-(2-phenoxyacetamido)-α-isopropenyl-2-oxoazetidine-1-acetate (2.0 g.) was dissolved in dry dioxane (60 cc), and iodine (0.51 g.) was added thereto. The mixture was stirred for 42 hours at room temperature and conentrated under reduced pressure. The residue was dissolved in ethyl acetate and the ethyl acetate solution was filtered. The filtrate was washed with a sodium thiosulfate aqueous solution and then with water, dried over magnesium sulfate, and concentrated. The residue was purified by subjecting it to a chromatography of silica gel in which chloroform was used as the eluant to give an oil (1.70 g.) of methyl 7-(2-phenoxyacetamido)-3-methyl-3-iodocepham-4-carboxylate.

Infrared spectrum:
1780, 1740, 1693 cm$^{-1}$

EXAMPLE 19

Methyl 4-(5-methyl-1,3,4-thiadiazole-2-yl)dithio-3-(2-phenoxyacetamido)-α-isopropenyl-2-oxoazetidine-1-acetate (123 mg.) was dissolved in absolute benzene (5 l cc) and thereto were added pyridine (40 mg.) and pyridinium hydrobromide perbromide (80 mg.). The mixture was stirred for 4 hours while heating slightly, washed with water and then a 5% aqueous solution of sodium carbonate, dried over magnesium sulfate and concentrated under reduced pressure. The residue was subjected to a chromatography of silica gel in which chloroform was used as the eluant and the eluate was concentrated to yield, as the residue, an amorphous material (70 mg.) of methyl 7-(2-phenoxyacetamido)-3-methyl-3-bromocepham-4-carboxylate.

This end product was identified by means of an Infrared spectrum and N.M.R. spectrum with that of Example 17.

The same end products were respectively obtained in a manner similar to that of Example 19 in which each of the following compounds instead of methyl 4-(5-methyl-1,3,4-thiadiazole-2-yl)dithio-3(2-phenoxyacetamido)-α-isopropenyl-2-oxoazetidine-1-acetate was used as the starting material.

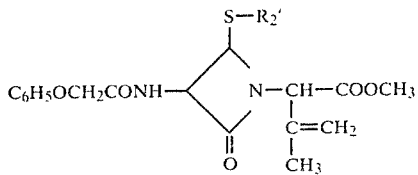

| Compound | R$_2$' | Property |
|---|---|---|
| a | benzylthio- | Oil |
| b | phenylthio- | Oil |
| c | thiazole-2-ylthio- | Oil |
| d | benzoxazole-2-ylthio- | Oil |
| e | quinoline-2-ylthio- | Oil |

EXAMPLE 20

A mixture of methyl 4-(5-methyl-1,3,4-thiadizole-2-yl)dithio-3-(2-phenoxyacetamido)-α-isopropenyl-2-oxoazetidine-1-acetate (247 mg.), N-bromosuccinimide (89 mg.) and absolute benzene (5 cc) was refluxed for 40 minutes. The reaction mixture was treated according to a manner similar to that of Example 19 to yield an amorphous material (130 mg.) of methyl 7-(2-phenoxyacetamido)-3-methyl-3-bromocepham-4-carboxylate.

This end product was identified by means of an Infrared spectrum and N.M.R. spectrum with that of Example 17.

EXAMPLE 21

4-(benzothiazole-2-yl)dithio-3-(2-phenoxyacetamido)-α-isopropenyl-2-oxoazetidine-1-acetic acid (1.03 g.) was dissolved in tetrahydrofuran (10 cc) and a carbon tetrachloride solution (1.6 g.) which contains 10 w/w% bromine was added thereto while cooling in an ice bath. The mixture was stirred for 6 hours at this same temperature and then filtered. The solvent of the filtrate was distilled off and the residue was dissolved in ethyl acetate. The ethyl acetate solution was washed with water, dried over magnesium sulfate and concentrated under reduced pressure to yield, as the residue, an amorphous material (0.8 g.) of 7-(2-phenoxyacetamido)-3methyl-3-bromocepham-4-carboxylic acid.

Infrared spectrum (Chloroform):
3400, 1780, 1739, 1690 cm$^{-1}$

EXAMPLE 22

A carbon tetrachloride solution (800 mg.) which contains 10 w/w% bromine was added, dropwise, to a mixture of methyl 4-(benzothiazole-2-yl)dithio-3-(2-phenoxyacetamido)-α-isopropenyl-2-oxoazetidine-1-acetate (530 mg.), acetamide (120 mg.) and tetrahydrofuran (5 cc) while cooling in an ice bath. The mixture was filtered one hour thereafter and the filtrate was concentrated under reduced pressure. The residue was dissolved in ethyl acetate and the ethyl acetate solution was washed in turn with water, a sodium bicarbonate solution and water, dried and concentrated to yield, as the residue, an amorphous material (430 mg.) of methyl 6-(2-phenoxyacetomide)-2-methyl-2-bromomethyl-penam-3-carboxylate.

Infrared spectrum:
3350, 1785, 1748, 1690 cm$^{-1}$

The following compounds were obtained in the same manner as described above.

2,2,2-trichloroethyl 6-amino-2-methyl-2-bromomethylpenam-3-carboxylate hydrochloride.

Infrared spectrum (Nujol):
3350-3400, 1790, 1770 cm$^{-1}$ 2,2,2-trichloroethyl 6-[2-(1H-tetrazole-1-yl)acetomido]-2-methyl-2-bromoethylpenam-3-carboxylate.
Infrared spectrum (Film):
3250, 1783, 1765, 1685 cm$^{-1}$ 2,2,2-trichloroethyl 6-[3-(2-chlorophenyl)-5-methylisoxazole-4-carbonamido]-2-methyl-2-bromoethylpenam-3-carboxylate.
Infrared spectrum (Film):
3370, 1790, 1765, 1670 cm$^{-1}$

EXAMPLE 23

The compounds listed in the right column of the following Table were obtained, respectively, by reacting the compound listed in the left column in a manner similar to those of the preceding Examples.

| Starting Products | End Products |
|---|---|
| 2,2,2-trichloroethyl 4-(benzothiazole-2-yl)dithio-3-[2-sydonone-3-yl)acetamido]-α-isopropenyl-2-oxoazetidine-1-acetate | 2,2,2-trichloroethyl 6-[2-(sydonone-3-yl)acetamido]-2-methyl-2-bromomethylpenam-3-carboxylate. Infrared spectrum (Nujol) 3300, 1780, 1750, 1700, 1640 cm$^{-1}$ |
| 2,2,2-trichloroethyl 4-(benzothiazole-2-yl)dithio-3-(2-cyanoacetamido)-α-isopropenyl-2-oxoazetidine-1-acetate | 2,2,2-trichloroethyl 7-(2-cyanoacetamido)-3-methyl-3-bromocepham-4-carboxylate. Infrared spectrum (Liquid Film) 3350, 1780, 1760, 1680 cm$^{-1}$ |
| 2,2,2-trichloroethyl 4-(benzothiazole-2-yl)dithio-3-[2-(p-hydroxyphenyl)-2-(1-cyclopropylethoxy)carbonylaminoacetamido]-α-isopropenyl-2-oxoazetidine-1-acetate | 2,2,2-trichloroethyl 6-[2-(p-hydroxyphenyl)-2-(1-cyclopropylethoxy)carbonylamino]-2-methyl-2-bromomethylpenam-3-carboxylate. Infrared spectrum (Nujol) 3300, 1785, 1765, 1675 cm$^{-1}$ |
| 2,2,2-trichloroethyl 4-(benzothiazole-2-yl)dithio-3-(2-cyanoacetamido)-α-isopropenyl-2-oxoazetidine-1-acetate | 2,2,2-trichloroethyl 6-(2-cyanoacetamido)-2-methyl-2-bromomethylpenam-3-carboxylate. Infrared spectrum (Liquid Film) 3300, 1780, 2250, 1765, 1690 cm$^{-1}$ |

Reaction of:

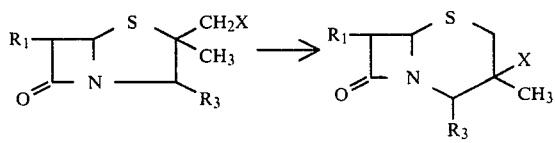

EXAMPLE 1

Methyl 6-(2-phenoxyacetamido)-2-methyl-2-bromoethylpenam-3-carboxylate (350 mg.) was dissolved in chloroform (10 cc), and then the mixture was allowed to stand for 4 days and purified by chromatography of silica gel to give an amorphous material (200 mg.) of methyl 7-(2-phenoxyacetamido)-3-bromo-3-methyl-cepham-4-carboxylate.

Infrared spectrum (Carbon tetrachloride):
3450, 1794, 1745, 1703 cm$^{-1}$

EXAMPLE 2

The compounds listed in the right column of the following Table were obtained, respectively, by reacting the compound listed in the left column in a manner similar to that of Example 1:

| Starting Products | End Products |
|---|---|
| Methyl 6-(2-phenoxyacetamido)-2-methyl-2-iodomethylpenam-3-carboxylate | Methyl 7-(2-phenoxyacetamido)-3-methyl-3-iodo-cepham-4-carboxylate, Infrared spectrum: 1780, 1740, 1693 cm$^{-1}$ |
| 6-(2-phenoxyacetamido)-2-methyl-2-bromomethylpenam-3-carboxylic acid | 7-(2-phenoxyacetamido)-3-methyl-3-bromocepham-4-carboxylic acid, Infrared spectrum: 3400, 1780, 1739, 1690 cm$^{-1}$ |
| 2,2,2-trichloroethyl 6-[2-(thiophene-2-yl)acetamido]-2-methyl-2-bromomethylpenam-3-carboxylate | 2,2,2-trichloroethyl 7-[2-(thiophene-2-yl)acetamido]-3-methyl-3-bromocepham-4-carboxylate. Infrared spectrum (Liquid Film) 3300, 1775, 1760, 1660 cm$^{-1}$ |

Reaction of:

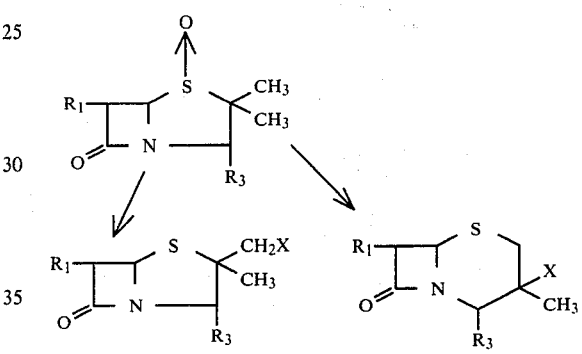

EXAMPLE 1

2,2,2-trichloroethyl 6-(2-phenylacetamido)-2,2-dimethylpenam-3-carboxylate-1-oxide (0.96 g.) was dissolved in 1,1,2-trichloroethane (15 cc), and pyridine (0.32 g.) and pyridine hydrochloride (0.12 g.) were added thereto. The mixture was heated at 100° C., for 3 hours, cooled, washed with water, dried and then concentrated. The residue was subjected to a chromatography of silica gel in which chloroform was used as the eluant. The eluate was concentrated to yield, as the residue, crystals (0.09 g.) of 2,2,2-trichloroethyl 6-(2-phenylacetamido)-2-methyl-2-chloromethylpenam-3-carboxylate, m.p. 104°-105° C.

EXAMPLE 2

Methyl 6-(2-phenoxyacetamido)-2,2-dimethylpenam-3-carboxylate-1-oxide (1.46 g.) was dissolved in 1,1,2-trichloroethane (20 cc) and pyridine (0.80 g.) and pyridine hydrochloride (0.24 g.) were added thereto. The mixture was heated at 95° C. for 6 hours, cooled, dried and concentrated. The residue was subjected to a chromatography of silica gel in which chloroform was used as the eluant. The eluate was concentrated to yield, as the residue, an oil (0.24 g.) of methyl 6-(2-phenoxyacetamido)-2-methyl-2-chloromethylpenam-3-carboxylate.

Infrared spectrum (Chloroform): 3400, 1788, 1747, 1690 cm$^{-1}$

EXAMPLE 3

2,2,2-trichloroethyl 6-[N-(2,2,2-trichloroethoxycarboxyl)phenylglycyl]amino-2,2-dimethylpenam-3-carboxylate-1-oxide (2.01 g.) was dissolved in 1,1,2-trichloroethane (15 cc), and then pyridine (0.6 g.) and pyridine hydrochloride (0.18 g.) were added thereto. The mixture was heated at 95° C. for 6 hours, and then treated in a manner similar to that of Example 1 to yield a powder (150 mg.) of 2,2,2-trichloroethyl 6-[N-(2,2,2-trichloroethoxycarbonyl)phenylglycyl]amino-2-methyl-2-chloromethylpenam-3-carboxylate, m.p. 90°–93° C. Reaction of:

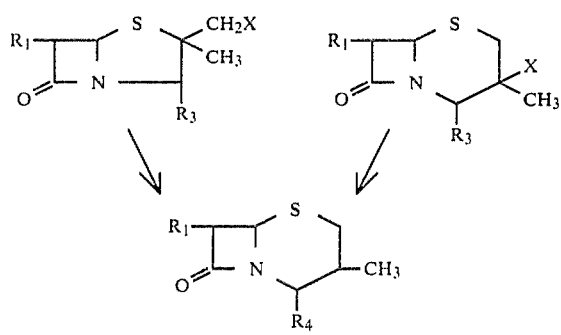

EXAMPLE 1

A mixture of methyl 7-(2-phenoxyacetamido)-3-methyl-3-bromocepham-4-carboxylate (210 mg.) in acetonitrile (5 cc) and anhydrous sodium acetate (100 mg.) was heated under reflux for 6.5 hours. The reaction mixture was concentrated under reduced pressure and the residue was dissolved in ethyl acetate. The solution washed with water, dried and then concentrated. The residue was crystallized from a mixture of ether and methanol to yield crystals (40 mg.) of methyl 7-(2-phenoxyacetamido)-3-methyl-3-cephem-4-carboxylate, m.p. 124°–125° C.

EXAMPLE 2

A mixture of methyl 7-(2-phenoxyacetamido)-3-methyl-3-iodocepham-4-carboxylate (0.25 g.) in dry acetonitrile (10 cc) and sodium acetate (45 mg.) was heated under reflux for 4 hours and concentrated. The residue was mixed with water and extracted with chloroform. The chloroform layer was washed with an aqueous sodium thiosulfate solution and then with water, dried and concentrated. The residue was subjected to chromatography on silica gel and eluated with chloroform to yield crystals (50 mg.) of methyl 7-(2-phenoxyacetamido)-3-methyl-3-cephem-4-carboxylate, m.p. 124°–125° C.

EXAMPLE 3

A solution of 7-(2-phenoxyacetamido)-3-methyl-3-bromocepham-4-carboxylic acid (860 mg.) in dry dichloroethane (20 cc) was cooled at −40°-−50° C. and pyridine and a 10% dichloromethane solution (4.7 g.) of thionyl chloride were respectively added thereto. The mixture was stirred at −40°-−50° C. for one hour and then at room temperature overnight, and poured into ice water and stirred for 30 minutes. The dichloroethane layer was extracted with an aqueous sodium bicarbonate solution and the aqueous layer was acidified with phosphoric acid and extracted with ethyl acetate. The ethyl acetate layer was washed with water, dried, treated with carbon powder and then concentrated to yield crystals (80 mg.) of 7-(2-phenoxyacetamido)-3-methyl-3-cephem-4-carboxylic acid, m.p. 172°–175° C.

EXAMPLE 4

A mixture of 2,2,2-trichloroethyl 6-(2-phenylacetamido)-2-methyl-2-bromomethylpenam-3-carboxylate (0.54 g.), chloroform (5 cc) and pyridine (0.16 g.) was heated under reflux for 2.5 hours. The reaction mixture was washed with water, dried over magnesium sulfate and then concentrated. The residue was crystallized from ether to yield crystals (0.34 g.) of 2,2,2-trichloroethyl 7-(2-phenylacetamido)-3-methyl-3-cephem-4-carboxylate, m.p. 161°–162° C.

EXAMPLE 5

A mixture of 2,2,2-trichloroethyl 6-[N-(2,2,2-trichloroethoxycarbonyl)phenylglycyl]amino-2-methyl-2-bromomethylpenam-3-carboxylate (0.43 g.), dry pyridine (0.09 g.) and dry chloroform (10 cc) was heated under reflux for 4.5 hours. The chloroform layer was separated, washed with water, dried and then concentrated. The residue was recrystallized from ether to yield needles (0.23 g.) of 2,2,2-trichloroethyl 7-[N-(2,2,2-trichloroethoxycarbonyl)phenylglycyl]amino-3-methyl-3-cephem-4-carboxylate, m.p. 99°–100.5° C.

EXAMPLE 6

A mixture of 2,2,2-trichloroethyl 6-(2-phenoxyacetamido)-2-methyl-2-bromomethylpenam-3-carboxylate (500 mg.), chloroform (10 cc) and pyridine (170 mg.) was heated under reflux for 10 hours. After cooling, the reaction mixture was washed with water, dilute phosphoric acid and water in order, dried and then concentrated. The residue was subjected to chromatography on silica gel and eluated to yield an oil. The oil was crystallized from a mixture of acetone and petroleum ether to yield 2,2,2-trichloroethyl 7-(2-phenoxyacetamido)-3-methyl-3-cephem-4-carboxylate, m.p. 111°–113° C.

EXAMPLE 7

6-(2-phenoxyacetamido)-2-methyl-2-bromomethylpenam-3-carboxylic acid (429 mg.) was suspended in dry benzene (10 cc), and pyridine (400 mg.) and trimethylsilylchloride (5 cc) were added thereto. The mixture was stirred for 1.5 hours at room temperature and pyridine (400 mg.) was added thereto. The mixture was heated under reflux for 3 hours, mixed with ethyl acetate (30 cc), washed with dilute phosphoric acid and further with an aqueous solution saturated with sodium chloride, dried and then concentrated. A small amount of ethyl acetate was added to the residue and the precipitate was collected by filtration to yield crystals (250 mg.) of 7-(2-phenoxyacetamido)-3-methyl-3-cephem-4-carboxylic acid, m.p. 170.5°–172° C.

EXAMPLE 8

A mixture of 2,2,2-trichloroethyl 6-(2-phenylacetamido)-2-methyl-2-chloromethylpenam-3-carboxylate (0.50 g.) in 1,1,2-trichloroethane (7 cc) and pyridine (0.16 g.) was heated under reflux for 3.5 hours. After cooling, the reaction mixture was washed with water, dried and then concentrated under reduced pressure. The residue was subjected to chromatography on silica gel and eluated with chloroform. The eluate was concentrated and the residue was crystallized with ether to yield crystals (0.12 g.) of 2,2,2-trichloroethyl 7-(2-phenylacetamido)-3-methyl-3-cephem-4-carboxylate, m.p. 161°–162° C.

EXAMPLE 9

The same end product as given in Example 8, 2,2,2-trichloroethyl 7-(2-phenylacetamido)-3-methyl-3-cephem-4-carboxylate, m.p. 161°–162° C. was obtained according to a similar manner to that of Example 8, by using 2,2,2-trichloroethyl 6-(2-phenylacetamido)-2-methyl-2-chloromethylpenam-3-carboxylate and picoline, dimethylaniline or quinoline instead of pyridine.

EXAMPLE 10

A solution of 1-cyclopropylethyl 6-(2-phenylacetamido)-2-methyl-2-bromomethylpenam-3-carboxylate (0.5 g.) and pyridine (0.20 g.) in benzene (12 cc) was heated under reflux for 3 hours. After cooling, the benzene layer was washed with water, dried and then concentrated. The residue was subjected to chromatography on silica gel to yield crystals (0.26 g.) of 1-cyclopropylethyl 7-(2-phenylacetamido)-3-methyl-3-cephem-4-carboxylate, m.p. 108°–112° C.

EXAMPLE 11

2,2,2-trichloroethyl 6-[2-(thiophene-2-yl)acetamido]-2-methyl-2-bromomethylpenam-3-carboxylate (0.85 g.) was dissolved in benzene (12 cc), and thereto was added pyridine (0.24 g.). The mixture was refluxed for 2 hours, washed with water, dried and concentrated. Ether was added to the residue and the precipitate was collected by filtration to yield crystals (0.41 g.) of 2,2,2-trichloroethyl 7-[2-(thiophene-2-yl)acetamido]-3-methyl-3-cephem-4-carboxylate, m.p. 151°–152° C.

EXAMPLE 12

4-hydroxy-3,5-di(tert)butylbenzyl 6-(2-phenylacetamido)-2-methyl-2-bromomethylpenam-3-carboxylate (0.12 g.) was dissolved in benzene (2 cc), and pyridine (0.032 g.) was added thereto. The mixture was refluxed for 2 hours and filtered. The filtrate was washed with water, dried and concentrated to yield, as the residue, a powder (0.074 g.) of 4-hydroxy-3,5-di(tert)-butylbenzyl 7-(2-phenylacetamido)-3-methyl-3-cephem-4-carboxylate.

Infrared spectrum: 1780, 1730, 1665 cm$^{-1}$

EXAMPLE 13

The following compounds were respectively obtained in a manner similar to those of the preceding Examples:

(a) Ester with acetoxime of 7-(2-phenoxyacetamido)-3-methyl-3-cephem-4-carboxylic acid, m.p. 188°–189° C.

(b) 2,2,2-trichloroethyl 7-[2-(1H-tetrazole-1-yl)acetamido)-3-methyl-3-cephem-4-carboxylate, m.p. 165°–167° C.

(c) 2,2,2-trichloroethyl 7-(2-acetoxy-2-phenylacetamido)-3-methyl-3-cephem-4-carboxylate.
Infrared spectrum (Chloroform): 3430, 1784, 1740, 1700 cm$^{-1}$ (d) Ester with 2-pyridinemethanol-1-oxide of 7-(2-phenylacetamido)-3-methyl-3-cephem-4-carboxylic acid.
Infrared spectrum (Nujol): 1770, 1725, 1678 cm$^{-1}$ (e) Ester with 2-pyridinemethanol-1-oxide of 7-[N-(2,2,2-trichloroethoxycarbonyl)phenylglycyl]amino-2-methyl-3-cephem-4-carboxylic acid.
Infrared spectrum (Nujol): 3300, 1780, 1730, 1685 cm$^{-1}$ (f) 7-(2-phenylacetamido)-3-methyl-3-cephem-4-carboxylic acid, m.p. 190°–194° C. (dec.).

(g) methylthiomethyl 7-(2-phenylacetamido)-3-methyl-3-cephem-4-carboxylate.
Infrared spectrum (Nujol): 3250, 1770, 1720, 1660 cm$^{-1}$ (h) 2-pyridylmethyl 7-(2-phenylacetamido)-3-methyl-3-cephem-4-carboxylate.
Infrared spectrum (Nujol): 3250, 1770, 1720, 1650 cm$^{-1}$ (i) 2,2,2-trichloroethyl 7-[N-(1,1-dimethylpropoxycarbonyl)-phenylglycyl]amino-3-methyl-3-cephem-4-carboxylate.
Infrared spectrum (Nujol): 3430, 1785, 1695 cm$^{-1}$ (j) 2,2,2-trichloroethyl 7-[N-(1-cyclopropylethoxycarbonyl)-phenylglycyl]amino-3-methyl-3-cephem-4-carboxylate, m.p. 111°–112° C.

(k) 7-[N-(1-cyclopropylethoxycarbonyl)phenylglycyl]-amino-3-methyl-3-cephem-4-carboxylic acid, m.p. 165°–170° C.

(l) p-nitrobenzyl 7-(2-phenylacetamido)-3-methyl-3-cephem-4-carboxylate, m.p. 191°–193° C.

(m) p-methoxybenzyl 7-(2-phenylacetamido)-3-methyl-3-cephem-4-carboxylate, m.p. 151°–152° C.

(n) Benzoylmethyl 7-(2-phenylacetamido)-3-methyl-3-cephem-4-carboxylate, m.p. 184°–190° C.

(o) p-bromobenzoylmethyl 7-(2-phenylacetamido)-3-methyl-3-cephem-4-carboxylate, m.p. 194°–198° C.

(p) t-butyl 7-(2-phenylzcetamido)-3-methyl-3-cephem-4-carboxylate, m.p. 120°–123° C.

(q) 2,2,2-trichloroethyl 7-[2-(sydonone-3-yl)acetamido]-3-methyl-3-cephem-4-carboxylate, m.p. 116°–119° C.

(r) 2,2,2-trichloroethyl 7-(2-cyanoacetamido)-3-methyl-3-cephem-4-carboxylate, m.p. 154°–159° C.

(s) 2,2,2-trichloroethyl 7-[2-(p-hydroxyphenyl)-2-(1-cyclopropylethoxy)carbonylaminoacetamido]-3-methyl-3-cephem-4-carboxylate.
Infrared spectrum (Liquid film): 3300, 1775, 1740, 1675 cm$^{-1}$ Many changes and modifications of the hereinbefore described reactions and products can be made or efected without departing from the spirit or scope of the invention. For instance, during the various reactions, if the $R_3$ or $R_4$ groups are carboxy radicals or carboxy derivative radicals, these radicals experience intermediate or complete conversion into other forms of carboxy or carboxy derivative radicals. For instance, if $R_3$ or $R_4$ is the radical COCl, the radical will be converted into —COOH. Similarly, if $R_3$ or $R_4$ is a carboxy radical, in the presence of a trimethylsilyl chloride, the carboxy group will be converted into a —COOSi(CH$_3$)$_3$ group, which can then be reconverted back to a —COOH group by treatment with water. Accordingly, it should be clearly understood that the invention is not to be construed as being limited except by the appended claims.

What is claimed and desired to be secured by Letters Patent is:

1. An oxoazetidine compound of the formula:

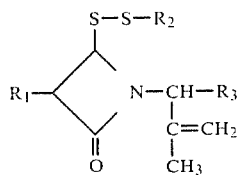

wherein R₁ is amino or amino substituted with a pharmaceutically acceptable carboxylic acyl protective group for the amino substituents in penicillin compounds, R₃ is a pharmaceutically acceptable carboxy, ester, acid amide, acid anhydride, acid halide, acid azide or salt of said carboxy group employed in penicillin compounds and R₂ is a pharmaceutically acceptable heterocyclic group selected from the group consisting of oxazolyl, benzoxazolyl, thiazolyl, benzothiazolyl, benzimidazolinyl, and imidazolizinyl, or said heterocyclic group substituted by lower alkyl radical, lower alkoxy radical, a halogen atom, a nitro radical, phenyl, tolyl, xylyl, chlorophenyl, nitrophenyl, benzyl, phenethyl, lower alkanoyl, benzoyl, phenylacetyl, thioacetyl, thiopropionyl, thiobenzoyl and phenyl thioacetyl.

2. An oxoazetidine compound of the formula:

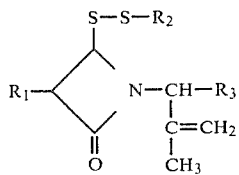

wherein R₁ represents unsubstituted amino or amino substituted by an acyl radical selected from the group consisting of formyl, acetyl, propionyl, butyryl, isobutyryl, valeryl, isovaleryl, pivaloyl, acryloyl, crotonoyl, 2-methylacryloyl, cyclopentylcarbonyl, cyclohexylcarbonyl, cycloheptylcarbonyl, cyclohexylacetyl, cycloheptylacetyl, cyclohexylpropionyl, cycloheptylpropionyl, dihydrobenzoyl, 2,4,6-cycloheptatrienylacetyl, dihydrophenylacetyl, methoxyacetyl, methylthioacetyl, 2-propenylthioacetyl, cyclohexylthioacetyl, cyclohexyloxyacetyl, dihydrophenoxyacetyl, dihydrophenylthioacetyl, cyclopentyloxycarbonyl, cyclohexyloxycarbonyl, dihydrophenoxycarbonyl, cycloheptyloxycarbonyl, benzoyl, toluoyl, naphthoyl, α-methylnaphthoyl, phthaloyl, tetrahydronaphthoyl, phenylacetyl, phenylpropionyl, phenylbutyryl, tolylacetyl, xylylacetyl, naphthylacetyl, tetrahydronaphthylacetyl, phenoxyacetyl, benzyloxycarbonyl, xylyloxycarbonyl, naphthoxycarbonyl, phenoxycarbonyl, 2-phenoxypropionyl and 2-phenoxybutyryl; carbonyl having thereon a heterocyclic compound selected from the group consisting of thiophene, benzothiophene, furan, pyran, isobenzofuran, chromene, xanthene, 2H-pyrrole, 3H-pyrrole, pyrrole, imidazole, pyrazole, pyridine, pyrimidine, pyrazine, pyridazine, isoindole, indole, indazole, quinoline, isoquinoline, isoxazole, oxadiazole, pyrrolidine, pyrroline, imidazolidine, piperidine, piperazine, diazole, triazole, oxazole, thiazole, tetrazole, benzoxazole, benzoxadiazole, benzothiazole, benzothiadiazole, benzotriazole, and benzimidazole, 1H(or 2H)-tetrazolylacetyl, thienylacetyl, thienylpropionyl, furylacetyl, piperazinylacetyl, pyrrolidinylacetyl, pyrrolidinylpropionyl, benzothiazolylacetyl, oxazolylacetyl, benzoxazolylacetyl, pyridylmethoxycarbonyl, 2-furyloxycarbonyl, 8-quinolyloxycarbonyl, the above-recited acyl radicals having at least one group thereon selected from the group consisting of methyl, ethyl, propyl, isopropyl, 1-propenyl, 2-propenyl, cyclopropyl, cyclopentyl, cyclohexyl, cycloheptyl, methoxy, ethoxy, propoxy, isopropoxy, methylthio, ethylthio, phenyl, xylyl, tolyl, benzyl, phenethyl, amino, mercapto, nitro, carboxy, hydroxy, chlorine, bromine, and fluorine, trichloroethoxycarbonyl, tribromoethoxycarbonyl, 1-cyclopropylethoxycarbonyl, 3-phenyl-5-methyl-4-oxazolylcarbonyl, 3-(2-chlorophenyl)-5-methyl-4-oxazolylcarbonyl, 3-(2,6-dichlorophenyl)-5-methyl-4-oxazolylcarbonyl, 3-(2-chloro-6-fluorophenyl)-5-methyl-4-oxazolylcarbonyl, 2-cyanoacetyl, 2-acetoxy-2-phenylacetyl, 2-(2-sydonone-3-yl)acetyl, said above-recited acyl having thereon an amino radical, wherein said amino radical is protected with a group selected from the group consisting of trichloroethoxycarbonyl, tribromoethoxycarbonyl, benzyloxycarbonyl, p-toluenesulfonyl, p-nitrobenzyloxycarbonyl, o-bromobenzyloxycarbonyl, o-nitrophenylsulfenyl, chloroacetyl, trifluoroacetyl, formyl, tertbutoxycarbonyl, p-methoxybenzyloxycarbonyl, 3,4-dimethoxybenzyloxycarbonyl, 4-phenylazobenzyloxycarbonyl, 4-(4-methoxyphenylazo)benzyloxycarbonyl, pyridine-1-oxide-2-methoxycarbonyl, 2-pyridylmethoxycarbonyl, 2-furyloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl, trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidiene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene, 1-methoxycarbonyl-2-propylidene, 2-ethoxycarbonylcyclohexylidene, 1-methoxycarbonyl-1-propene-2-yl, and 2-ethoxycarbonyl-1-cyclohexenyl, the above recited acyl having thereon a hydroxy or mercapto group wherein said hydroxy or mercapto group is protected with a group selected from the group consisting of benzyloxycarbonyl, 4-nitrobenzyloxycarbonyl, 4-methoxybenzyloxycarbonyl, 3,4-dimethoxybenzyloxy-carbonyl, 4-phenylazobenzyloxycarbonyl, 4-(4-methoxyphenylazo)-benzyloxycarbonyl, tert-butoxycarbonyl, 1,1-dimethylpropoxycarbonyl, isopropoxycarbonyl, diphenylmethoxycarbonyl, 2-pyridylmethoxycarbonyl, 2,2,2-trichloroethoxycarbonyl, 2,2,2-tribromoethoxycarbonyl, 3-iodopropoxycarbonyl, 2-furfuryloxycarbonyl, 1-adamantyloxycarbonyl, 1-cyclopropylethoxycarbonyl, 8-quinolyloxycarbonyl, trifluoroacetyl, benzyl, trityl, methoxymethyl, 2-nitrophenylthio, and 2,4-dinitrophenylthio, and the above recited acyl having thereon a carboxy group wherein said carboxy group is protected with an ester selected from the group consisting of methyl ester, ethyl ester, propyl ester, isopropyl ester, tertbutyl ester, butyl ester, benzyl ester, diphenylmethyl ester, triphenylmethylester, p-nitrobenzyl ester, p-methoxybenzyl ester, benzoylmethyl ester, acetylmethyl ester, p-nitrobenzoylmethyl ester, p-bromobenzoylmethyl ester, p-methanesulfonylbenzoylmethyl ester, phthalimidomethyl ester, trichloroethyl ester, tribromoethyl ester, 1,1-dimethyl-2-propynyl ester, acetoxymethyl ester, propionyloxymethyl ester, pivaloyloxymthyl ester, 1,1-dimethylpropyl ester, 1,1-dimethyl-2-propenyl ester, 3-methyl-3-butenyl ester, succinimidomethyl ester, 1-cyclopropylethyl ester, 3,5-di(tert)butyl-4-hydroxybenzyl ester, methylsulfenylmethyl ester, phenylsulfenylmethyl ester, methylthiomethyl ester, phenylthiomethyl ester, dimethylaminomethyl ester, quinoline-1-oxide-2-methyl ester, pyridine-1-oxide-2-methyl ester, and di(p-methoxyphenyl)methyl ester; $R_3$ is (a) carboxy, (b) an ester selected from the group consisting of methyl ester, ethyl ester, propyl ester, isopropyl ester, butyl ester, tert-butyl ester, cyclohexyl ester, cycloheptyl ester, vinyl ester, 1-propenyl ester, 2-propenyl ester, 3-butenyl ester, phenyl ester, xylyl ester, tolyl ester, naphthyl ester, benzyl ester, phenethyl ester, methoxymethyl ester, ethoxymethyl ester, methylthioethyl ester, methylthiomethyl ester, dimethylaminoethyl ester, diethylaminoethyl ester, phenoxymethyl ester, phenylthiomethyl ester, methylsulfenylmethyl ester, phenylsulfenylmethyl ester, benzoylmethyl ester, toluoylmethyl ester, chloromethyl ester, bromomethyl ester, trichloroethyl ester, cyanomethyl ester, p-nitrophenyl ester, 2,4,5-trichlorophenyl ester, 2,4,6-trichlorophenyl ester, pentachlorophenyl ester, p-methanesulfonylphenyl ester, 4-phenylazophenyl ester, 2,4-dinitrophenyl ester, p-chlorobenzyl ester, o-nitrobenzyl ester, p-methoxybenzyl ester, p-nitrobenzyl ester, 3,4,5-trimethoxybenzyl ester, bis(p-methoxyphenyl)methyl ester, pentachlorobenzyl ester, trichlorobenzyl ester, 3,5-di(tert)butyl-4-hydroxybenzyl ester, p-nitrophenylthiomethyl ester, p-nitrobenzoylmethyl ester, p-bromobenzoylmethyl ester, 2-pyridylmethyl ester, p-chlorobenzoylmethyl ester, and the ester formed by the reaction of said carboxy with a compound selected from the group consisting of N-hydroxysuccinimide, N-hydroxyphthalimide, tetrahydrofuran, 1-cyclopropylethanol, 1-phenyl-3-methyl-5-pyrazolone, 3-hydroxypyridine, 2-hydroxymethylpyridine-1-oxide, 1-hydroxy-2-(1H)-pyridine, dimethylhydroxyamine, diethylhydroxyamine, glycolamide, 8-hydroxyquinoline, 2-hydroxymethylquinoline-1-oxide, acetoxime, methoxyacetylene, ethoxyacetylene, tert-butylethynyldimethylamine, tert-butylethynyldiethylamine, ethylethynyldiethylamine, and 2-ethyl-5-(3-sulfophenyl)isoxazolium hydroxide inner salt;

(c) an acid amide selected from the group consisting of N-methyl acid amide, N-ethyl acid amide, N,N-dimethyl acid amide, N,N-diethyl acid amide, N-methyl-N-ethyl acid amide, and an acid amide with imidazole;

(d) an acid anhydride formed by reaction of said carboxy radical with a compound selected from the group consisting of dibenzyl phosphate, phosphoric acid, sulfuric acid, pivalic acid, pentanoic acid, isopentanoic acid, 2-ethylbutanoic acid, chloroacetic acid, crotonic acid, valeric acid, propionic acid, 3-chloro-2-pentanoic acid, 3-bromo-2-buteneoic acid, phenylacetic acid, phenoxyacetic acid, furaneacetic acid, thiopheneacetic acid and benzoic acid;

(e) an acid halide selected from the group consisting of acid chloride and acid bromide;

(f) an acid azide; or (g) a carboxy salt selected from the group consisting of a sodium salt, potassium salt, magnesium salt, methylamine salt, diethylamine salt, trimethylamine salt, aniline salt, pyridine salt, picoline salt, and N,N'-dibenzylethylenediamine salt and $R_2$ is a heterocyclic group selected from the group consisting of imidazolizinyl, benzimidazolizinyl, benzothiazolyl, benzoxazolyl, and thiatriazoyl, oxazolyl, or said heterocyclic group substituted by alkyl selected from the group consisting of methyl and ethyl; alkoxy selected from the group consisting of methoxy and ethoxy; halogen selected from the group consisting of chlorine, bromine and fluorine; nitro; aryl selected from the group consisting of phenyl, tolyl and xylyl; substituted aryl selected from the group consisting of chlorophenyl and nitrophenyl; aralkyl selected from the group consisting of benzyl and phenethyl; or acyl selected from the group consisting of acetyl, propionyl, benzoyl, phenylacetyl, thioacetyl, thiopropionyl, thiobenzoyl and phenylthioacetyl.

3. The compound of claim 1, wherein said amino group is protected by a radical selected from the group consisting of trichloroethoxycarbonyl, tribromoethoxycarbonyl, benzyloxycarbonyl, p-toluenesulfonyl, p-nitrobenzyloxycarbonyl, o-bromobenzyloxycarbonyl, o-nitrophenylsulfenyl, chloroacetyl, trifluoroacetyl, formyl, tert-butoxycarbonyl, p-methoxybenzyloxycarbonyl, 3,4-dimethoxybenzyloxycarbonyl, 4-(4-methoxyphenylazobenzyloxycarbonyl, 4-(4-methoxyphenylazo)benzyloxycarbonyl, pyridine-1-oxide-2-methoxycarbonyl, 2-pyridylmethoxycarbonyl, 2-furyloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl, trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene and mono or disilyl.

4. The compound of claim 1, wherein said group $R_3$ as an ester is selected from the group consisting of methyl, ethyl, propyl, isopropyl, butyl, tert-butyl, cyclohexyl, cycloheptyl, vinyl, 1-propenyl, 2-propenyl, 3-butenyl, phenyl, xylyl, tolyl, naphthyl, benzyl, phenethyl, methoxymethyl, ethoxymethyl, methylthioethyl, methylthiomethyl, dimethylaminoethyl, diethylaminoethyl, phenoxymethyl, phenylthiomethyl, methylsulfenylmethyl, phenylsulfenylmethyl, benzoylmethyl, toluoylmethyl, chloromethyl, bromomethyl, trichloroethyl, cyanomethyl, p-nitrophenyl, 2,4,5-trichlorophenyl, 2,4,6-trichlorophenyl, pentachlorophenyl, p-methanesulfonylphenyl, 4-phenylazophenyl, 2,4-dinitrophenyl, p-chlorobenzyl, o-nitrobenzyl, p-methoxybenzyl, p-nitrobenzyl, 3,4,5-trimethoxyphenyl, bis(p-methoxyphenyl)methyl, pentachlorobenzyl, trichlorobenzyl, 3,5-di(tert)butyl-4-hydroxybenzyl, p-nitrophenylthiomethyl, p-nitrobenzoylmethyl, and p- chlorobenzoylmethyl ester or is an ester formed from a thioalcohol, a substituted thioalcohol, N-hydroxysuccinimide, N-hydroxyphthalimide, tetrahydrofuran, 1-cyclopropylethanol, 1-phenyl-3-methyl-5-pyrazolone, 3-hydroxypyridine, 2-hydroxymethylpyridine-1-oxide, 1-hydroxy-2(1H)-pyridine, dimethylhydroxyamine, diethylhydroxyamine, glycolamide, 8-hydroxyquinoline, 2-hydroxymethylquinoline-1-oxide, oxime, methoxyacetylene, ethoxyacetylene, tert-butylethynyldimethylamine, tert-butylethynyldiethylamine, ethylethynyldiethylemine or 2-ethyl-5-(3-sulfophenyl)isoxazolium hydroxide inner salt.

5. The compound of claim 1, wherein said group $R_3$ as an amide is selected from the group consisting of N-methyl, N-ethyl, N,N-dimethyl, N,N-diethyl and N-methyl-N-ethylamide or is an amide of imidazole or 4-substituted imidazole.

6. The compound of claim 1, wherein said group $R_3$ as an acid anhydride is selected from the group consisting of dialkyl phosphate, dibenzyl phosphate, phosphoric acid, sulfuric acid, alkyl carbonate, pivalic acid, pentanoic acid, isopentanoic acid, 2-ethylbutanoic acid, chloroacetic acid, crotonic acid, valeric acid, propionic acid, 3-chloro-2-pentanoic acid, 3-bromo-2-butenoic acid, phenylacetic acid, phenoxyacetic acid, furanacetic acid, thiophenacetic acid and benzoic acid anhydride or is a symmetric acid anhydride.

7. The compound of claim 1, wherein said group $R_3$ as a carboxy salt is selected from the group consisting of sodium, potassium, magnesium, methylammonium, diethylammonium, trimethylammonium, anilinium, pyridinium, picolinium and N,N-dibenzylethylenediammonium salts.

8. The compound of claim 1, wherein said heterocyclic group is substituted by at least one substituent selected from the group consisting of methyl, ethyl, methoxy, ethoxy, fluorine, chlorine, bromine, nitro, phenyl, tolyl, xylyl, chlorophenyl, nitrophenyl, benzyl, phenethyl, acetyl, propionyl, benzoyl, phenylacetyl, thioacetyl, thiopropionyl, thiobenzoyl and phenylthioacetyl.

9. The oxoazetidine derivative compound of claim 1, wherein $R_1$ represents cyano(lower)alkanoylamino, phenyl(lower)alkanoylamino, phenoxy(lower)alkanoylamino, phenyl(lower)alkanoylamino substituted by lower alkoxycarbonylamino, phenyl(lower)alkanoylamino substituted by trihalo(lower)alkoxycarbonylamino, hydroxyphenyl(lower)alkanoylamino substituted by lower alkoxycarbonylamino, thienyl(lower)alkanoylamino, sydronyl(lower)alkanoylamino or lower alkoxycarbonyl(lower)alkylideneamino, $R_3$ represents carboxy, lower alkyl ester, trihalo(lower)alkyl ester, phenyl(lower)alkyl ester substituted by hydroxy and two lower alkyl groups or ester with acetoxime and $R_2$ represents thiazolyl, thiazolyl substituted by lower alkyl, or benzoxazolyl.

10. The oxazetidine derivative compound of claim 9, wherein $R_1$ represents 2-cyanoacetamido, 2-phenylacetamido, 2-phenoxyacetamido, N-tertiarybutoxycarbonylphenylglycylamino, N-(2,2,2-trichloroethoxycarbonyl) phenylglycylamino, N-(1-cyclopropylethoxycarbonyl)phenylglycylamino, 2-(p-hydroxyphenyl)-2-(1-cyclopropylethoxy)carbonylaminoacetamido, 2-(thiophene-2-yl)acetamido, 2-(sydron-3-yl)acetamido or 1-ethoxycarbonyl-1-propene-2-ylamino, $R_3$ represents carboxy, methyl ester, 1-cyclopropylethyl ester, 2,2,2-trichloroethyl ester, 4-hydroxy-3,5-ditertiarybutylbenzyl ester or ester with acetoxime and $R_2$ represents thiazole-2-yl, or benzoxazole-2-yl.

11. The oxazetidine derivative compound of claim 10, which is 2,2,2-trichloroethyl 4-(benzoxozole-2-yl)dithio-3-(2-phenylacetamido)-α-isopropenyl-2-oxoazetidine-1-acetate.

12. The oxazetidine derivative compound of claim 10, which is methyl 4-(thiazole-2-yl)dithio-3-(2-phenoxyacetamido)-α-isopropenyl-2-oxoazetidine-1-acetate.

13. The oxazetidine derivative compound of claim 10, which is methyl 4-(benzoxazole-2-yl)dithio-3-(2-phenoxyacetamido)-α-isopropenyl-2-oxoazetidine-1-acetate.

* * * * *

UNITED STATES PATENT AND TRADEMARK OFFICE
CERTIFICATE OF CORRECTION

PATENT NO. : 4,267,340
DATED : May 12, 1981
INVENTOR(S) : TAKASHI KAMIYA ET AL

It is certified that error appears in the above—identified patent and that said Letters Patent is hereby corrected as shown below:

Please correct the Priority Data to read as follows:

[30]--Foreign Application Priority Data

Jun. 24, 1971 [JP]    Japan......46-46158

Aug. 14, 1971 [JP]    Japan......46-61776

Aug. 14, 1971 [JP]    Japan......46-61777

Aug. 18, 1971 [JP]    Japan......46-62687

Aug. 21, 1971 [JP]    Japan......46-63885

Aug. 21, 1971 [JP]    Japan......46-63886

UNITED STATES PATENT AND TRADEMARK OFFICE
CERTIFICATE OF CORRECTION

PATENT NO. : 4,267,340

DATED : May 12, 1981

INVENTOR(S) : TAKASHI KAMIYA ET AL

It is certified that error appears in the above—identified patent and that said Letters Patent is hereby corrected as shown below:

Sept. 9, 1971 [JP]   Japan......46-70018

Dec. 23, 1971 [JP]   Japan......47-2516 --- rather than

[30]--Foreign Application Priority Data

Jun. 24, 1971 [JP]   Japan......46-46158

Aug. 14, 1971 [JP]   Japan......46-61776

Aug. 14, 1971 [JP]   Japan......46-61777

Aug. 18, 1971 [JP]   Japan......46-62687

Aug. 21, 1971 [JP]   Japan......46-63885

Aug. 21, 1971 [JP]   Japan......46-63886--- as it now appears

Signed and Sealed this

Thirteenth Day of October 1981

[SEAL]

Attest:

GERALD J. MOSSINGHOFF

Attesting Officer

Commissioner of Patents and Trademarks